US008557893B2

(12) United States Patent
Yang et al.

(10) Patent No.: US 8,557,893 B2
(45) Date of Patent: Oct. 15, 2013

(54) SUBSTITUTED SACCHARIDE COMPOUNDS AND DENTAL COMPOSITIONS

(75) Inventors: Jie Yang, Woodbury, MN (US); Sumita B. Mitra, West St. Paul, MN (US); Yi He, Roseville, MN (US); Brian A. Shukla, Woodbury, MN (US); Naimul Karim, Maplewood, MN (US); Afshin Falsafi, Woodbury, MN (US); Richard B. Ross, Cottage Grove, MN (US); Paul R. Klaiber, Mahtomedi, MN (US); George W. Griesgraber, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/813,673

(22) PCT Filed: Aug. 19, 2011

(86) PCT No.: PCT/US2011/048383
§ 371 (c)(1),
(2), (4) Date: Feb. 1, 2013

(87) PCT Pub. No.: WO2012/036838
PCT Pub. Date: Mar. 22, 2012

(65) Prior Publication Data
US 2013/0164709 A1     Jun. 27, 2013

Related U.S. Application Data

(60) Provisional application No. 61/383,080, filed on Sep. 15, 2010.

(51) Int. Cl.
*A61K 6/083* (2006.01)
*C07C 233/20* (2006.01)

(52) U.S. Cl.
USPC .................. 523/116; 564/208; 526/238.23

(58) Field of Classification Search
USPC .................. 564/208; 526/238.23; 523/116
See application file for complete search history.

(56) References Cited

U.S. PATENT DOCUMENTS

| | | | |
|---|---|---|---|
| 2,776,951 A | 1/1957 | Melamed | |
| 4,503,169 A | 3/1985 | Randklev | |
| 4,642,126 A | 2/1987 | Zador | |
| 4,652,274 A | 3/1987 | Boettcher | |
| 4,787,850 A | 11/1988 | Michl | |
| 5,130,347 A | 7/1992 | Mitra | |
| 5,185,466 A * | 2/1993 | Kozulic et al. | 564/208 |
| 5,438,092 A | 8/1995 | Kozulic | |
| 5,480,790 A * | 1/1996 | Tischer et al. | 435/188 |
| 5,545,676 A | 8/1996 | Palazzotto | |
| 5,814,407 A | 9/1998 | Richard | |
| 6,387,981 B1 | 5/2002 | Zhang | |
| 6,552,103 B1 * | 4/2003 | Bertozzi et al. | 523/106 |
| 6,572,693 B1 | 6/2003 | Wu | |
| 6,624,236 B1 | 9/2003 | Bissinger | |
| 6,730,156 B1 | 5/2004 | Windisch | |
| 6,852,795 B2 | 2/2005 | Bissinger | |
| 6,852,822 B1 | 2/2005 | Bissigner | |
| 6,887,920 B2 | 5/2005 | Ohtsuki | |
| 7,090,721 B2 | 8/2006 | Craig | |
| 7,090,722 B2 | 8/2006 | Budd | |
| 7,156,911 B2 | 1/2007 | Kangas | |
| 7,241,437 B2 | 7/2007 | Davidson | |
| 7,632,098 B2 | 12/2009 | Falsafi | |
| 7,649,029 B2 | 1/2010 | Kolb | |
| 7,674,850 B2 | 3/2010 | Karim | |
| 8,329,674 B2 | 12/2012 | Yang | |
| 2006/0147394 A1 | 7/2006 | Shastry | |
| 2006/0204452 A1 | 9/2006 | Velamakanni | |
| 2007/0253916 A1 | 11/2007 | Maitra | |
| 2007/0264509 A1 | 11/2007 | Lai | |
| 2008/0003252 A1 | 1/2008 | Lai | |
| 2008/0004410 A1 | 1/2008 | Lai | |
| 2008/0197324 A1 | 8/2008 | Zhao | |
| 2008/0300340 A1 | 12/2008 | Gross | |
| 2010/0150847 A1 | 6/2010 | Yang | |

FOREIGN PATENT DOCUMENTS

| | | |
|---|---|---|
| DE | 102 04 234 A1 * | 8/2003 |
| EP | 0115410 | 8/1984 |
| EP | 0383023 | 8/1990 |
| EP | 367886 | 4/1995 |
| EP | 0650974 | 5/1995 |
| EP | 0709402 | 5/1996 |
| EP | 2108663 | 10/2009 |
| EP | 2112177 | 10/2009 |
| EP | 2133368 | 12/2009 |

(Continued)

OTHER PUBLICATIONS

International Search Report PCT/US2011/048383; May 8, 2012; 7 pgs.
Larpent, et al., "Macrocyclic sugar-based surfactants: block molecules combining self-aggregation and complexation properties", (2004) Abstract, 3 pgs.
Furhop et al., "Two polymeric micellar fibers with gluconamide head groups", (1991) abstract, 2 pgs.
Melamed, Amides of Vinyl Ethers Containing Hydroxyl Groups, and Polymers Thereof, (1957), abstract, 2 pgs.
Hamade et al., "D-gluconamide derivatives for preparing lipid-coated enzymes and antifouling marine paint compositions", (1997), abstract, 5 pgs.
Ladmiral et al., "Synthetic Glycopolymers: an overview", European Polymer Journal 40 (2004) 431-449.
Varma et al., "Synthetic Polymers Functionalized by Carbohydrates: a review", Carbohydrate Polymers 56 (2004) 429-445.

(Continued)

Primary Examiner — Tae H Yoon
(74) Attorney, Agent, or Firm — Carolyn A. Fischer

(57) ABSTRACT

Substituted saccharide compounds, dental compositions comprising substituted saccharide compounds, and methods of using dental compositions are described. In one embodiment, the substituted saccharide amide compound comprises a hydrophobic group and at least one free-radically polymerizable group with the proviso that the hydrophobic group is not bonded to the ethylenically unsaturated carbon atom of the free-radically polymerizable group. The hydrophobic group is typically bonded to a nitrogen atom of a saccharide amine residue or a carbonyl moiety of saccharide amide residue.

44 Claims, No Drawings

(56) References Cited

FOREIGN PATENT DOCUMENTS

| | | |
|---|---|---|
| GB | 2306473 | 5/1997 |
| JP | 61268192 | 11/1986 |
| JP | 5-65159 | 9/1993 |
| JP | 06242532 | 9/1994 |
| JP | 7316098 | 12/1995 |
| JP | 10-72404 | 3/1998 |
| JP | 2000-109501 | 4/2000 |
| WO | WO 99/64563 | 12/1999 |
| WO | WO 00/38169 | 6/2000 |
| WO | WO 01/30305 | 5/2001 |
| WO | WO 01/30306 | 5/2001 |
| WO | WO 01/30307 | 5/2001 |
| WO | WO 03/063804 | 8/2003 |
| WO | WO 2008/033911 | 3/2008 |
| WO | WO 2008/047812 | 4/2008 |
| WO | WO 2008/098019 | 8/2008 |
| WO | WO 2009/054492 | 4/2009 |
| WO | WO 2011/126647 | 10/2011 |

OTHER PUBLICATIONS

Inouye et al., "Some Fatty Acid Derivatives of D-Glucosamine", Biochemical Laboratory, College of Argiculture, Kyoto University; vol. 78; Apr. 24, 1956; 4722-4724.

Griffin, "Calculation of HLB Values of Non-Ionic Surfactants" Journal of the Society of Cosmetic Chemists; 249-256.

Borman, "New Approach to Glycosylation", Chemical & Engineering News, vol. 83, No. 34, Aug. 22, 2005, 2 pags.

Borman, "Carbohydrate Advances"; Chemical & Engineering News, vol. 83, No. 32, Aug. 8, 2005; pp. 41-50.

Borman, "Key Oligosaccharide of Cell Wall Prepared"; Chemical & Engineering News: Science & Technology; vol. 83, No. 38, p. 38; Sep. 19, 2005.

Borman, "Drug Candidates March OnWard", ACS Meeting News, Chemical & Engineering News: Science & Technology; Sep. 26, 2005, vol. 83, No. 39, pp. 39-41.

Borman, "Carbohydrate Vaccines", Chemical & Engineering News, vol. 82, No. 32, Aug. 9, 2004, pp. 31-35.

Wynn, "Aloe ver gel: Update for Dentistry", Pharmacology Today, Jan.-Feb. 2005; pp. 6-9.

Lei, "Biomimetic Surfaces of Biomaterials Using Mucin-Type Glycoproteins", Trends in Glycoscience and Glycotechnology, vol. 12, No. 66 (Jul. 2000) pp. 229-239.

Bamford et al., "Chemical Modification of Polymers Intended to Increase Blood Compatibility", Bull. Soc. Chim. Belg., vol. 99, (1990), pp. 919-930.

Tello et al., "In vitro evaluation of complex carbohydrate denture adhesive formulations", Prosthodontics, Quintessence International, vol. 29, No. 9 (1998), pp. 585-593.

Borman, "Cancer Vaccine Is Best in Class", Chemical & Engineering News: Latest News, vol. 83, No. 37 (Sep. 12, 2005) p. 10.

Denny, "Novel Test for Caries Risk, Application of a Scientific Principle", 3M ESPE Jan. 16, 2007, 29 pgs.

Paulson, "Functional Glycomics: Decoding the Glycome", The Scripps Research Institute, 23 pgs. (Undated).

Matsunaga et al., "Chitosan Monomer Promotes Tissue Regeneration on Dental Pulp Wounds", Division of Cariology, Nagasaki University Graduate School of Biomedical Sciences, (2005) pp. 711-720.

Tarsi et al., "Inhibition of *Streptococcus mutans* Adsorption to Hydroxyapatite by Low-molecular-weight Chitosans", Journal of Dental Research, (1997) 76(2): 665-672.

Olden et al., "Role of carbohydrate in biological function of the adhesive glycoprotein fibronectin", Proc. Natl. Acad. Sci. USA, vol. 76, No. 7, pp. 3343-3347 (Jul. 1979) Cell Biology.

Smart, "Lectin-mediated drug delivery in the oral cavity", Advanced Drug Delivery Reviews 56 (2004) 481-489.

* cited by examiner

# US 8,557,893 B2

SUBSTITUTED SACCHARIDE COMPOUNDS AND DENTAL COMPOSITIONS

BACKGROUND

WO 2008/033911 describes dental composition comprising organogelators, product and methods. A suitable and preferred class of organogelators is that of amino sugars, including linear amine sugars and cyclic amino sugars.

EP2108663 relates to a hydrophilic polymerizable monomer that is used mainly for dental material and that has a plurality of polymerizable groups; a polymerizable composition containing the polymerizable monomer; and dental material using the composition, such as dental primers, bonding materials, cements, and composite resins.

EP2112177 relates to a composition, suitable for a dental composition containing a polymerizable monomer having at least two polymerizable groups and at least two hydroxyl groups; and water.

SUMMARY

Presently described are substituted saccharide compounds, dental compositions comprising substituted saccharide compounds, and methods of using dental compositions.

In one embodiment, a substituted saccharide amide compound is described. The substituted saccharide amide compound comprises a hydrophobic group and at least one free-radically polymerizable group with the proviso that the hydrophobic group is not bonded to the ethylenically unsaturated carbon atom of the free-radically polymerizable group. The hydrophobic group is typically bonded to a nitrogen atom of a saccharide amine residue or a carbonyl moiety of saccharide amide residue.

In other embodiments, dental compositions are described. In one favored embodiment, the dental composition is highly acidic and suitable for use as a (e.g. self-etching) adhesive, cement, sealant, or flowable composite restoration material. The dental composition comprises 35 wt-% to 75 wt-% of ethylenically unsaturated compounds with acid functionality and at least one free-radically polymerizable substituted saccharide compound, such as the saccharide amide compounds previously described. The dental composition can be applied to a (e.g. hard) dental tissue surface without pretreating the surface with an etchant or primer.

In other embodiments, a dental composition suitable for use as a restoration is described comprising at least one free-radically polymerizable substituted saccharide compound and appreciable amounts of inorganic oxide (e.g. nanocluster) filler.

DETAILED DESCRIPTION

As used herein, "dental composition" refers to a material, optionally comprising filler, capable of adhering or being bonded to an oral surface. A curable dental composition can be used to bond a dental article to a tooth structure, form a coating (e.g. sealant) on a tooth surface, or can be used to fabricate a preformed (e.g. crown or bridge) restorative. Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., orthodontic sealants), and varnishes. The curable dental composition may also be a composite (also referred to as restorations) such as a dental fillings, as well as dental articles such as crowns, bridges, and articles for dental implants. Highly filled dental compositions are also used for mill blanks, from which a crown may be milled. A composite is a highly filled paste designed to be suitable for filling substantial voids in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding a dental restoration such as a crown, bridge, or implant.

As used herein, "adhesive" or "dental adhesive" refers to a composition used as a pre-treatment on a dental structure (e.g., a tooth) to adhere a dental material (e.g., restorative), a dental article (e.g. crown), or an orthodontic appliance (e.g., bracket)) to a dental structure.

In some embodiments, the dental structure surface can be pre-treated, e.g., by etching, priming, and/or applying an adhesive to enhance the adhesion with the dental material.

As used herein, an "etchant" refers to an acidic composition that is capable of fully or partially solubilizing (i.e., etching) a dental structure surface. The etching effect can be visible to the naked human eye and/or instrumentally detectable (e.g., by light microscopy). Typically, an etchant is applied to the dental structure surface for a period of about 10 to 30 seconds.

As used herein, a "self-etching" composition refers to a composition that bonds to a dental structure surface without pretreating the dental structure surface with an etchant. Preferably, a self-etching composition can also function as a self-primer wherein no primer is used.

As used herein, a "hard tissue surface" refers to tooth structures (e.g., enamel, dentin, and cemented) and bone.

As used herein, "dental article" refers to an article that can be adhered (e.g., bonded) to a tooth structure or dental implant. Dental articles include, for example, crowns, bridges, veneers, inlays, onlays, fillings, orthodontic appliances and devices.

As used herein, "orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

As used herein, an "oral surface" refers to a soft or hard surface in the oral environment. Hard surfaces typically include tooth structure including, for example, natural and artificial tooth surfaces, bone, and the like.

As used herein, "hardenable" is descriptive of a material or composition that can be cured (e.g., polymerized or crosslinked) by heating to induce polymerization and/or crosslinking; irradiating with actinic irradiation to induce polymerization and/or crosslinking; and/or by mixing one or more components to induce polymerization and/or crosslinking "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

As used herein, "hardened" refers to a material or composition that has been cured (e.g., polymerized or crosslinked).

As used herein, "hardener" refers to something that initiates hardening of a resin. A hardener may include, for example, a polymerization initiator system, a photoinitiator system, a thermal initiator and/or a redox initiator system.

When the substituted saccharide compound is utilized in dental compositions that are cured by exposure to (ultraviolet) radiation, the polymerizable group is a free-radically polymerizable group such as (meth)acrylate, acrylate, vinyl, styryl. The term "(meth)acrylate" is a shorthand reference to acrylate, methacrylate, or combinations thereof; "(meth) acrylic" is a shorthand reference to acrylic, methacrylic, or combinations thereof; and "(meth)acryl" is a shorthand reference to acryl, methacryl, or combinations thereof.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

As used herein, "substituted saccharide amide compound" refers to all compound derived from a saccharide compound.

A carbohydrate is an organic compound with the general formula $C_m(H_2O)_n$. The term carbohydrate is a term commonly used in biochemistry and is a synonymous with the term saccharide. Carbohydrates (saccharides) are divided into four chemical groupings: monosaccharides, disaccharides, oligosaccharides, and polysaccharides.

Monosaccharides are the simplest carbohydrates in that they cannot be hydrolyzed into smaller carbohydrates. Monosaccharides are aldehydes or ketones with two or more hydroxyl groups. The general chemical formula of an unmodified monosaccharide is $(C.H_2O)_n$. The smallest monosaccharides, for which n=3, are dihydroxyacetone and D- and L-glyceraldehyde.

Monosaccharides are classified according to three different characteristics, i.e. location of the carbonyl group, the number of carbon atoms, and stereochemistry. If the carbonyl group is an aldehyde, the monosaccharide is an aldose; whereas if the carbonyl group is a ketone, the monosaccharide is a ketose. Monosaccharide with three carbon atoms are called trioses, those with four are called tetroses, five are called pentoses, six are hexoses, and so on. These two classification systems are often combined. For example, glucose is an aldohexose (a six-carbon aldehyde), ribose is an aldopentose (a five-carbon aldehyde), and fructose is a ketohexose (a six-carbon ketone). Each carbon atom bearing a hydroxyl group (—OH), with the exception of the first and last carbons, are asymmetric, making them stereocenters with two possible configurations each (R or S). Because of this asymmetry, a number of isomers may exist for any given monosaccharide formula.

Two joined monosaccharides are disaccharides, the simplest polysaccharide. The two monosaccharide units are bound together by a covalent bond known as a glycosidic linkage, formed via a dehydration reaction, resulting in the loss of a hydrogen atom from one monosaccharide and a hydroxyl group from the other. Unsubstituted disaccharides have the general formula is $C_{12}H_{22}O_{11}$. Although there are numerous kinds of disaccharides, sucrose is the most common disaccharide. It is composed of one D-glucose molecule and one D-fructose molecule. Another common disaccharide is lactose, composed of one D-galactose molecule and one D-glucose molecule.

In some embodiments, the substituted saccharide amide compound described herein is derived from a sugar alcohol, and thus comprises a sugar alcohol residue. A sugar alcohol (also known as a polyol, polyhydric alcohol, or polyalcohol) is a hydrogenated form of carbohydrate wherein its carbonyl group (aldehyde or ketone) has been reduced to a primary or secondary alcohol. Hence, a sugar alcohol is a residue of a saccharide compound.

In general, the monosaccharides, disaccharides, and sugar alcohols are lower molecular weight carbohydrates. Hence the substituted saccharide compounds derived from such are also relatively low in molecular weight. The molecular weight is typically at least 250 or 300 g/mole and no greater than 1200 g/mole. In some embodiments, the molecular weight is no greater than 1000 or 800 g/mole.

The substituted saccharide amide compounds described herein comprise a hydrophobic group and at least one free-radically polymerizable group. The hydrophobic group is not bonded to the ethylenically unsaturated carbon atom of the free-radically polymerizable group. Hence, the hydrophobic group is not a residue of or derived from a long chain alkyl (meth)acrylate. The substituted saccharide amide compound described herein can be described as amphiphilic free-radically polymerizable monomers. Such monomers comprise hydrophilic groups that include hydroxyl groups and/or acid groups and a hydrophobic group in the same molecule.

Amphiphilic compounds can be characterized by various methodology. One common characterization method, as known in the art, is the hydrophilic-lipophilic balance ("HLB"). Although various method have been described for determining the HLB of a compound, as used herein, HLB refers to the value obtained by the Griffin's method (See Griffin W C: "Calculation of HLB Values of Non-Ionic Surfactants," Journal of the Society of Cosmetic Chemists 5 (1954): 259). The computations were conducted utilizing the software program Molecular Modeling Pro Plus from Norgwyn Montgomery Software, Inc. (North Wales, Pa.).

According to Griffin's method:

$$HLB=20*Mh/M$$

where Mh is the molecular mass of the hydrophilic portion of the molecule, and M is the molecular mass of the whole molecule. This computation provides a numerical result on a scale of 0 to 20, wherein "0" is highly lipophilic.

The following table depicts the HLB number of various substituted saccharide compounds, as described herein, along with the HLB number of the same compound excluding the hydrophobic group.

Hydrophilic-Lipophilic Balance of Polymerizable Saccharide Compounds

|  | Mol. Wt. HLB | Molecular Weight (g/mole) |
|---|---|---|
| N-Methyl-N-Octanoyl Glucamide Dimethacrylate | 11.9 | 631.7 |
| N-Methyl-N-Octanoyl Glucamide Dimethacrylate without $(CH_2)_6CH_3$ Hydrophobic Group | 15.3 | 533.5 |
| Change in HLB/Molecular Weight by inclusion of hydrophobic group | −3.4 | +98.2 |
| N-Octyl Acryloyl Glucamide | 11.6 | 347.5 |
| N-Octyl Acryloyl Glucamide without $(CH_2)_7CH_3$ Hydrophobic Group | 18.6 | 235.3 |
| Change in HLB/Molecular Weight by inclusion of hydrophobic group | −7 | +112.2 |
| N-Octyl Acryloyl Glucamide Phosphate | 13.6 | 507.4 |
| N-Octyl Acryloyl Glucamide Phosphate without $(CH_2)_7CH3$ Hydrophobic Group | 19.5 | 395.2 |
| Change in HLB/Molecular Weight by inclusion of hydrophobic group | −5.9 | +112.2 |
| N-Dodecanoyl Cyclic Glucamide Dimethacrylate | 10.9 | 671.8 |
| N-Dodecanoyl Cyclic Glucamide Dimethacrylate without $(CH_2)_{10}CH3$ Hydrophobic Group | 16.2 | 517.5 |
| Change in HLB/Molecular Weight by inclusion of hydrophobic group | −5.3 | +154.4 |

As is evident from the table above, the inclusion of the hydrophobic group renders the substituted saccharide compound sufficiently lipophilic such that the substituted saccharide amide compound has an HLB decrease of at least 2 or 3. In some embodiments, the HLB is decreased by at least 4 or 5. In yet other embodiments, the HLB is decreased by greater than 5. For example, the HLB decrease may be 6, 7, or 8. Such decrease in HLB is relative to the same compound in the absence of such hydrophobic group.

As is also evident from the table above, the inclusion of the hydrophobic group increases the molecular weight by at least 50 or 75 g/mole. In some embodiments, the increase in molecular weight is at least 100 g/mole or 150 g/mole. As athe chain length of the hydrophobic group increases, the increase in molecular weight may be at least 200 g/mole, or 250 g/mole, or 300 g/mole.

In some embodiments, the HLB of the substituted saccharide compounds is at least 10, or 11, or 12, or 13, or 14. In some embodiments, the HLB is at least 15 or 16. Further, in some embodiments the HLB is at least 17, or 18, or 19. However, as the chain length of the (e.g. alkyl) hydrophobic group increases, the HLB decreases. Hence, as the chain length approaches 26 carbon atoms, the HLB may be as low as 9, or 8, or 7, or 6, or 5.

The hydrophobic group of the saccharide amine compound is typically an alkyl group. Unless specified otherwise, "alkyl" includes straight-chained, branched, and cyclic alkyl groups and includes both unsubstituted and substituted alkyl groups. The alkyl group generally comprises at least four carbons atoms and preferably at least five carbon atoms. As the chain length of the alkyl group increases, the hydrophobicity increases, provided the alkyl group lack hydrophilic substituents. In some embodiments, the alkyl group comprises at least 6, 7, or 8 carbon atoms. The alkyl group typically comprises no greater than twenty-six carbon atoms. In some embodiments, the alkyl group comprises a straight chain alkyl group. In other embodiments, the alkyl group comprises a branched alkyl group. In still other embodiments, the alkyl group comprises a cyclic alkyl group. Non-limiting examples of alkyl groups include butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

The alkyl group may optionally comprise other substituents. In some embodiments, such substituents may be hydrophobic substituents. However, hydrophilic substituents may optionally be present, provided that the substituted alkyl group is sufficiently hydrophobic such that the saccharide amide compound has an HLB increase of at least 2, as previously described.

The polymerizable substituted saccharide compounds described can be derived from a saccharide starting compound that comprises a saccharide group and a hydrophobic group in the same molecule. The polymerizable saccharide compounds described herein are typically derived from a saccharide amine or saccharide amide compound. The hydrophobic (e.g. alkyl) group is typically bonded to a nitrogen atom of a residue of a saccharide amine or a carbonyl moiety of a residue of a saccharide amide.

In some embodiment, the polymerizable saccharide compound comprises a hydrophobic group bonded to the nitrogen atom of a saccharide amine residue.

Such saccharide compound may have the general formula:

In this general formula, $R_1$ is a hydrophobic group. $R_2$ is a free-radically polymerizable group. $R_3$ is independently hydrogen or an acidic group. In some embodiment, n is an integer ranging from 1 to 4.

In some embodiments, each $R_3$ is hydrogen. Such saccharide compounds comprise hydroxyl groups, yet lack acidic groups. In other embodiments, at least one of the $R_3$ groups is an acidic group. Hence, in this embodiment, the compound typically comprises a combination of both hydroxyl and acidic hydrophilic groups. In yet other embodiments, each $R_3$ is an acidic group. In this embodiment, all the hydroxyl groups of the saccharide moiety have been substituted with acid groups.

Various alkyl saccharide amines may be used to derive the saccharide amide compound. The polymerizable saccharide compound may be derived from, and thus comprise a residue of, an alkyl glucamine, including for example N-methyl-N-octanoyl-D-glucamine, N-methyl-N-nonanoyl-D-glucamine, N-methyl-N-decanoyl-D-glucamine, N-octyl-D-glucamine, and N-methyl-N-octyl-D-glucamine. Alkyl saccharide amines can be reacted with acryloyl chloride thereby forming a (meth)acrylate group bonded to the nitrogen atom of the amine residue.

Illustrative compounds are depicted as follows:

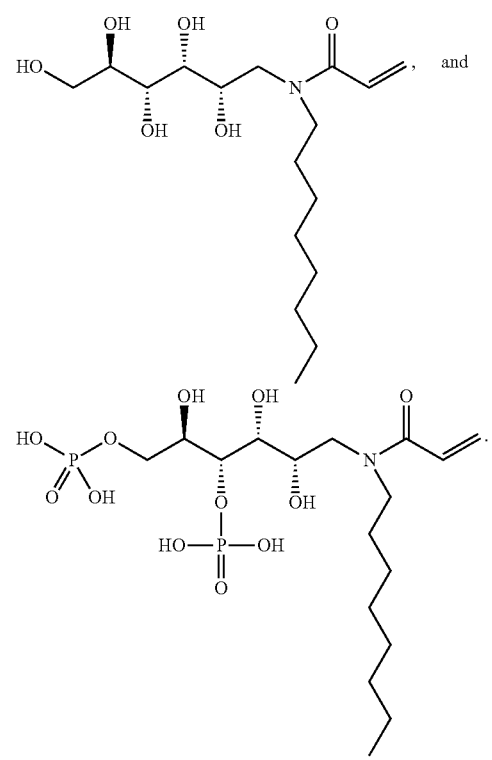

In other embodiments, the saccharide amide compound comprises a hydrophobic group bonded to the carbonyl moiety a saccharide amide residue.

Such saccharide compound may have the general formula

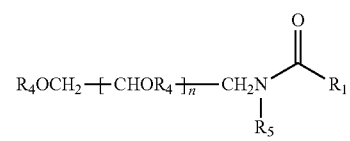

In this general formula, $R_1$ is a hydrophobic group. $R_4$ is independently hydrogen, an acidic group, or -L-$R_2$ wherein L is a linking group and $R_2$ is a free-radically polymerizable group with the proviso that at least one $R_4$ is -L-$R_2$. $R_5$ is hydrogen or a $C_1$-$C_4$ alkyl group. In some embodiments, n is an integer ranging from 1 to 4. In some embodiments, at least two $R_4$ groups are -L-$R^2$.

Illustrative compounds are depicted as follows:

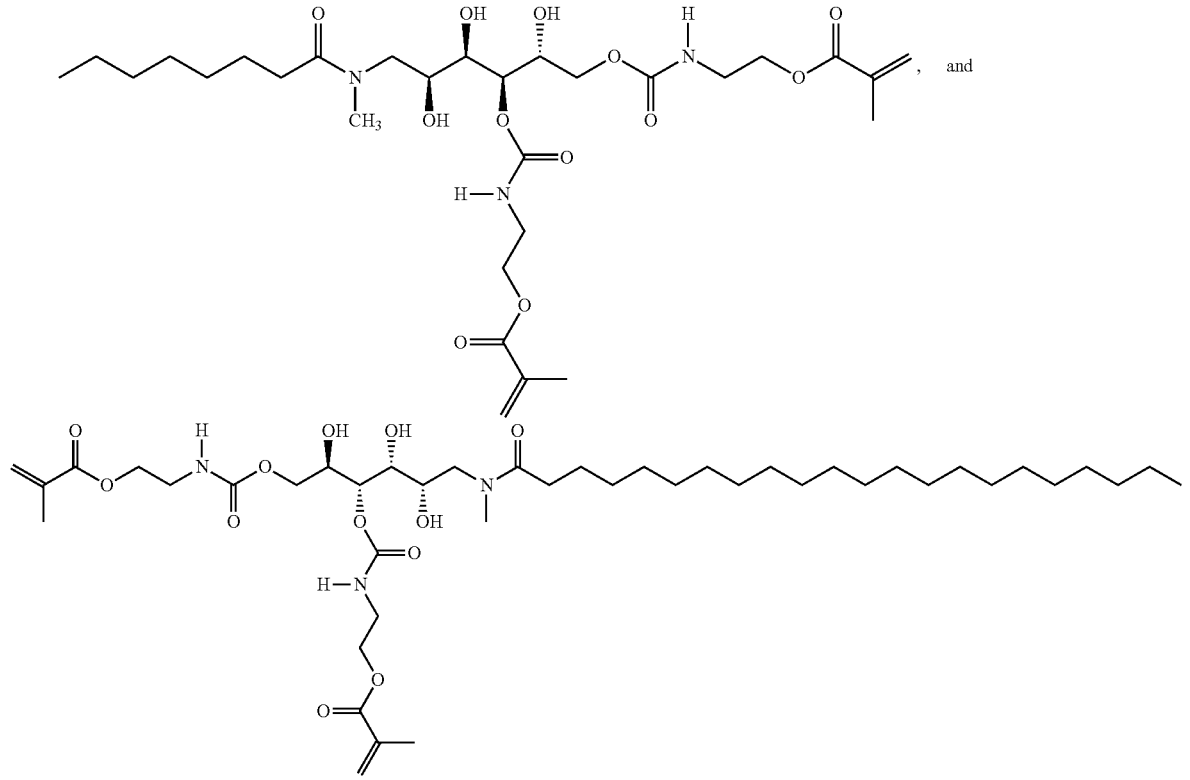

In yet another embodiment, the polymerizable substituted saccharide amide compound has a cyclic structure. Such substituted saccharide amide may have the general formula

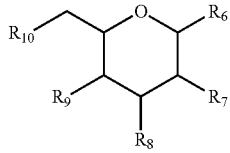

In this general formula, at least one of $R_6$-$R_{10}$ is

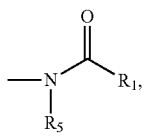

wherein $R_5$ is hydrogen or a $C_1$-$C_4$ alkyl group and $R_1$ is a hydrophobic group. Further, at least one of $R_6$-$R_{10}$ is O-L-$R_2$, wherein O is oxygen and L is a linking group. $R_2$ is a free-radically polymerizable group. The remaining $R_6$-$R_{10}$ substituents are OH or an acidic group.

In some embodiments, at least two of the $R_6$-$R_{10}$ substituents are O-L-$R^2$. In some embodiments, the remaining $R_6$-$R_{10}$ substituents are OH and thus the substituted saccharide compounds lacks acidic groups.

An illustrative compound is depicted as follows:

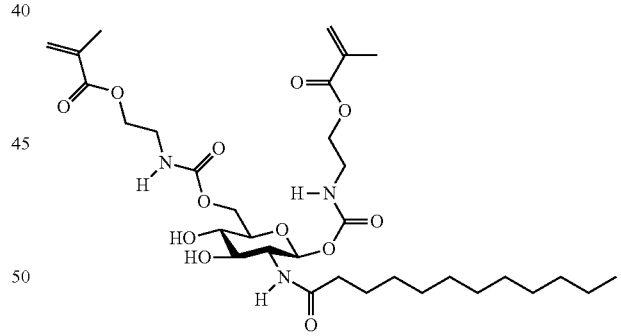

The substituted saccharide amide compounds that comprises a hydrophobic group bonded to the carbonyl moiety of a saccharide amide residue can be derived by reacting an alkyloyl saccharide amide with a compound having both isocyanate functionality and (meth)acrylate functionality, such as 2-isocyanatoethyl methacrylate. The isocyanate functional group reacts with one or more hydroxyl groups of the sacharride residue resulting in the saccharide amide comprising one or more (meth)acrylate end group bonded to the saccharide core via urethane linkages.

In each of the substituted saccharide amide formulas described herein, the hydrophobic group is typically a $C_5$ to $C_{26}$ alkyl group. In some embodiments, the alkyl group comprises at least 6, 7 or 9 carbon atoms. Further in some embodiments, alkyl group comprises no greater than 20, or 18, or 16, or 14, or 12 carbon atoms. The alkyl group may comprise optionally substituents, as previously described.

In some embodiments, the substituted saccharide (e.g. amide) compound comprises a (e.g. free-radically) polymerizable group, a saccharide residue, a hydrophobic group, and one or more acidic groups in the same molecule. Such compounds can be synthesized by further reacting a portion of or all the hydroxyl groups of the saccharide moiety with an acid chloride compound. The hydroxyl groups are preferably substituted with a phosphoric, phosphonic, sulfuric, or carboxylic acidic group. In some embodiments, the acidic group is a phosphoric or phosphonic acid group.

The polymerizable dental compositions described herein comprise one or more free-radically polymerizable substituted saccharide compounds, such as the saccharide (e.g. amide) compounds comprising a hydrophobic group and optionally acidic groups as described herein.

The polymerizable saccharide compound may be present in the curable dental composition at a concentration of 1 to 99.95 wt-% of the dental composition.

In some embodiments, the polymerizable saccharide compound described herein provides improved adhesion to oral (e.g. hard) tissue surfaces, particularly dentin. Depending on the desired improvement in adhesive, the concentration of the polymerizable saccharide compound may vary. In some embodiments, the concentration of the polymerizable saccharide (e.g. amide) compound is at least 2 wt-% or 3 wt-% or 4 wt-% of the dental composition. To reduce cost, one may employ as low of a concentration as necessary to obtain the desired (e.g. increased adhesion) effect. However, the polymerizable saccharide (e.g. amide) compound may be utilized at higher concentrations. The concentration of the polymerizable saccharide (e.g. amide) can be at least 6 wt-% or 7 wt-% or 8 wt-% of the dental composition. The concentration of the polymerizable saccharide (e.g. amide) compound is typically no greater than 40 wt-% or 50 wt-% of the dental composition. In some favored (e.g. self-etching) adhesive embodiments, the concentration of (e.g. multifunctional) saccharide (e.g. amide) compound typically ranges from about 5 wt-% to 15 wt-% or 20 wt-% of the dental composition.

In some embodiments, the polymerizable saccharide compounds described herein having acidic groups, particularly mono(meth)acrylate species, can be utilized as a primer in the absence of further comprising other ethylenically unsaturated (e.g. (meth)acrylate) monomers. In other embodiments, dental adhesive compositions can be prepared from multi(meth) acrylate saccharide compounds having acidic groups in the absence of further comprising other ethylenically unsaturated (e.g. (meth)acrylate) monomers. In these embodiments, the dental composition lacks other ethylenically unsaturated compounds. As used herein "other ethylenically unsaturated compounds" refers to all ethylenically saturated compounds that are not substituted polymerizable saccharide compounds. Hence sorbital dimethacrylate is considered an "other ethylenically unsaturated compound" since although sorbital dimethacrylate is a polymerizable saccharide compound, such compound lacks a (e.g. hydrophobic or acidic) substituent.

Alternatively or in combination with providing improved adhesion, the polymerizable saccharide (e.g. amide) compound may be utilized in place of conventional (meth)acrylate monomer that are commonly used in curable dental compositions. For example, the polymerizable saccharide (e.g. amide) compound may be utilized in place of hardenable components comprising hydroxyl group(s) and ethylenically unsaturated (e.g. (meth)acrylate) group(s) in a single molecule, such as 2-hydroxylethyl methacrylate (HEMA) and 2,2-bis[4-(2-hydroxy-3-methacryloyloxy-propoxy)phenyl] propane (BisGMA). As yet another example, the dental composition may comprise one or more polymerizable saccharide (e.g. amide) compounds having acidic groups in place of other ethylenically unsaturated monomers having acid functionality.

In some embodiments, the dental composition comprises one or more mono(meth)acrylate saccharide (e.g. amide) compounds having a single free-radically polymerizable group in place of other mono(meth)acrylate monomers, such as HEMA.

In yet other embodiments, the dental composition may comprise one or more saccharide (e.g. amide) compounds having at least two free-radically polymerizable groups. Due to the multi-functionality of such compounds, such saccharide compounds can replace (at least a substantial portion of) other multi-functional (meth)acrylate monomers that would typically be present in a dental composition such as (Bis-GMA).

In addition to the polymerizable saccharide compound described herein, the curable component of the polymerizable dental composition can include a wide variety of other ethylenically unsaturated compounds (with or without acid functionality), epoxy-functional (meth)acrylate resins, vinyl ethers, glass ionomer cements, and the like.

The (e.g., photopolymerizable) dental compositions may include compounds having free radically reactive functional groups that may include monomers, oligomers, and polymers having one or more ethylenically unsaturated group. Examples of useful ethylenically unsaturated compounds include acrylic acid esters, methacrylic acid esters, hydroxy-functional acrylic acid esters, hydroxy-functional methacrylic acid esters, and combinations thereof.

In some embodiments, the dental (e.g. composite) composition comprises a greater amount of other ethylenically unsaturated compound(s). For example, the weight ratio of the total amount of polymerizable substituted saccharide compound(s) to other ethylenically unsaturated compounds may range from about 1:5 to about 1:25.

In other embodiment, the dental (e.g. composite) composition comprises a greater or equal amount of polymerizable substituted saccharide compound(s). For example, the weight ratio of the total amount of polymerizable substituted saccharide compound(s) to other ethylenically unsaturated compounds may range from about 5:1 to about 1:1.

In some embodiments, the dental (e.g. restoration) compositions described herein comprise one or more hardenable components in the form of ethylenically unsaturated compounds without acid functionality.

In some embodiments, the dental composition is an aqueous dental adhesive comprising the adhesion promoting polymerizable saccharide amide compound and other polymerizable organic component and dispersed in water and a cosolvent such as ethanol or isopropyl alcohol. In such embodiments, the other polymerizable organic component comprises water dispersible polymeric film formers. Some saccharide compounds, such as the multi (meth)acrylate compounds (e.g. of Example 1) exhibit film-forming properties, and thus can replace film-forming components in aqueous dental (e.g. adhesive) compositions.

In another embodiment, the dental adhesive composition is non-aqueous, including less than 1%, more preferably less than 0.5%, and most preferably less than 0.1% by weight water. In this embodiment, the polymerizable components of the adhesive composition need not be water dispersible.

Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate (TEGDMA), 1,3-propanediol di(meth)acrylate, trimethylolpropane tri(meth)acrylate (e.g. TMPTMA), 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates (e.g. UDMA); the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.). Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.). Mixtures of two or more free radically polymerizable compounds can be used if desired. Suitable ethylenically unsaturated compounds are also available from a wide variety of commercial sources, such as Sigma-Aldrich, St. Louis, Mo.

In some embodiments, the polymerizable dental composition comprises tri-(meth)acrylate isocyanurate monomer as described in U.S. Provisional Application Ser. No. 61/319,534, filed Mar. 31, 2010. Such (meth)acrylate monomers may have the general structure

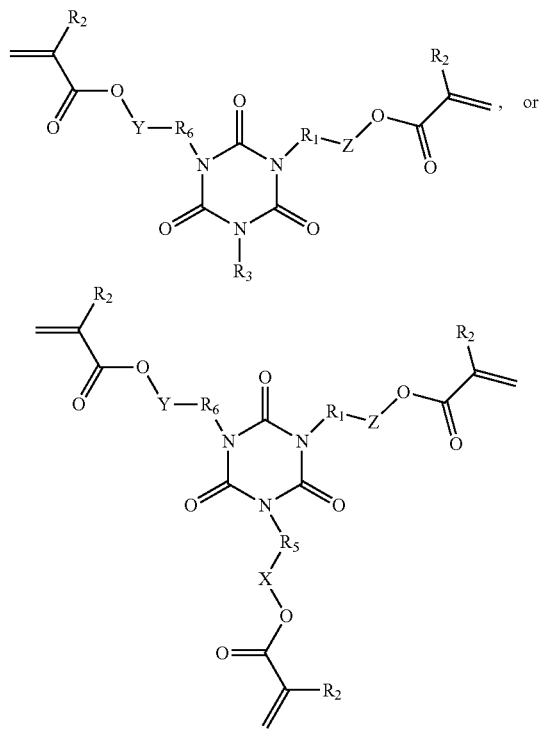

wherein
$R_1$, $R_5$, and $R_6$ are independently alkylene, arylene, or alkarylene, optionally including a heteroatom (e.g. oxygen, nitrogen, or sulfur);

$R_2$ is hydrogen or methyl; X, Y, and Z are independently alkylene, arylene, or alkarylene linking groups, comprising a heteroatom;
$R_3$ is independently hydrogen, alkyl, aryl, or alkaryl, optionally including a heteroatom; and
$R_2$ is hydrogen or methyl.

$R_1$ is typically an alkylene, optionally including a heteroatom, having no greater than 12 carbons atoms. In some favored embodiments, $R_1$ has no greater than 8, 6, or 4 carbon atoms. In some favored embodiments, $R_1$, $R_5$, $R_5$ comprise a hydroxyl moiety.

In some embodiments, Z comprises an aliphatic or aromatic diester linkage.

In some embodiment, Z further comprises one or more ether moieties. Hence, the linking group may comprise a combination of ester or diester moieties and one or more ether moieties.

$R_1$ is generally derived from the starting (e.g. hydroxyl terminated) isocyanurate precursor. Various isocyanurate precursor materials are commercially available from TCI America, Portland, Oreg.

The (e.g. self-etching adhesive) polymerizable dental composition preferably comprises a hardenable component comprising a hydroxyl group(s) and ethylenically unsaturated group(s) in a single molecule. Examples of such materials include hydroxyalkyl (meth)acrylates, such as 2-hydroxyethyl (meth)acrylate (HEMA) and 2-hydroxypropyl (meth) acrylate; glycerol mono- or di-(meth)acrylate (e.g. GDMA); trimethylolpropane mono- or di-(meth)acrylate; pentaerythritol mono-, di-, and tri-(meth)acrylate; sorbitol mono-, di-, tri-, tetra-, or penta-(meth)acrylate (e.g. sorbital DMA), and 2,2-bis[4-(2-hydroxy-3-methacryloyloxy-propoxy)phenyl] propane (BisGMA).

The) polymerizable dental compositions described herein preferably comprise one or more hardenable components in the form of ethylenically unsaturated compounds with acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, alpha, beta-unsaturated acidic compounds such as glycerol phosphate mono(meth)acrylates, glycerol phosphate di(meth)acrylates, hydroxyethyl (meth)acrylate phosphates (i.e. HEMA-phosphate), bis ((meth)acryloxyethyl)phosphate, ((meth)acryloxypropyl) phosphate, bis((meth)acryloxypropyl)phosphate, bis((meth) acryloxy)propyloxy phosphate, (meth)acryloxyhexyl phosphate, bis((meth)acryloxyhexyl)phosphate (MHP), (meth)acryloxyoctyl phosphate, bis((meth)acryloxyoctyl) phosphate, (meth)acryloxydecyl phosphate, bis((meth)acryloxydecyl)phosphate, caprolactone methacrylate phosphate, citric acid di- or tri-methacrylates, poly(meth)acrylated oligomaleic acid, poly(meth)acrylated polymaleic acid, poly (meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable component system. Also monomers, oligomers, and polymers of unsaturated carbonic acids such as (meth)acrylic acids, aromatic (meth)acrylated acids (e.g., methacrylated trimellitic acids), and anhydrides thereof can be used. Other ethylenically unsaturated compounds with acid functionality are known in the art such as described in previously cited US 2006/0204452.

The dental compositions typically comprise at least 35 wt-% or 36 wt-% or 37 wt-% or 38 wt-% or 39 wt-% or 40 wt-% and no greater than 75 wt-% of ethylenically unsaturated compounds with acid functionality, based on the total weight of the dental composition. In some embodiments, the concentration of ethylenically unsaturated compounds with acid functionality is at least 45 wt-% or 50 wt-%. In some embodiments, the concentration of ethylenically unsaturated compounds with acid functionality is at least 55 wt-% or 60 wt-%. Ethylenically unsaturated compounds with acid functionality having at least one P—OH moiety, such as HEMA-phosphate, MHP, and combination thereof, are typically preferred.

Inclusion of a high concentration of ethylenically unsaturated compounds with acid functionality renders the dental composition highly acidic. The pH of the composition is typically less than 3 or 2. In some favored embodiments, the pH is less than 1.

The acidic dental compositions find utility as (e.g. self-etching) sealants, adhesives, cements, or flowable composite restoration.

The acidic dental compositions may further comprise at least 5 wt-% up to about 55 wt-% of other ethylenically unsaturated compounds without acid functionality. In some embodiments, the amount of other ethylenically unsaturated compounds without acid functionality is no greater than 25 wt-%.

In some embodiments, the adhesive composition further comprises a photocurable ionomer, i.e. a polymer having pendent ionic groups capable of a setting reaction and pendent free radically polymerizable groups to enable the resulting mixture to be polymerized, i.e., cured, upon exposure to radiant energy. In some embodiments, the (e.g. adhesive) composition lacks photocurable ionomers. In other embodiments, the (e.g. adhesive) composition comprises a small concentration photocurable ionomer for the purpose of increasing the dentin adhesion. The concentration of photocurable ionomer typically ranges from at least 0.1 wt-% or 0.2 wt-% up to 2 wt-%, 3 wt-%, 4 wt-% or 5 wt-%.

As described for example in U.S. Pat. No. 5,130,347, photocurable ionomers have the general formula:

$$B(X)_m(Y)_n$$

wherein
B represents an organic backbone,
each X independently is an ionic group,
each Y independently is a photocurable group,
m is a number having an average value of 2 or more, and
n is a number having an average value of 1 or more.

Preferably the backbone B is an oligomeric or polymeric backbone of carbon-carbon bonds, optionally containing non-interfering substituents such as oxygen, nitrogen or sulfur heteroatoms. The term "non-interfering" as used herein refers to substituents or linking groups that do not unduly interfere with either the photocuring reaction of the photocurable ionomer.

Preferred X groups are acidic groups, with carboxyl groups being particularly preferred.

Suitable Y groups include, but are not limited to, polymerizable ethylenically unsaturated groups and polymerizable epoxy groups. Ethylenically unsaturated groups are preferred, especially those that can be polymerized by means of a free radical mechanism, examples of which are substituted and unsubstituted acrylates, methacrylates, alkenes and acrylamides.

X and Y groups can be linked to the backbone B directly or by means of any non-interfering organic linking group, such as substituted or unsubstituted alkyl, alkoxyalkyl, aryl, aryloxyalkyl, alkoxyaryl, aralkyl, or alkaryl groups.

Preferred photocurable ionomers are those in which each X is a carboxyl group and each Y is an ethylenically unsaturated group such as a (meth)acrylate group that can be polymerized by a free radical mechanism. Such ionomers are conveniently prepared by reacting a polyalkenoic acid (e.g., a polymer of formula $B(X)_{m+n}$ wherein each X is a carboxyl group) with a coupling compound containing both an ethylenically unsaturated group and a group capable of reacting with a carboxylic acid group such as an NCO group. The resulting photocurable ionomer preferably has least one of the free radically polymerizable (e.g. (meth)acrylate group)) is linked to said ionomer by means of an amide linkage. The molecular weight of the resultant photocurable ionomers is typically between about 1000 and about 100,000 g/mole.

In certain embodiments, the compositions are photopolymerizable, i.e., the compositions contain a photoinitiator (i.e., a photoinitiator system) that upon irradiation with actinic radiation initiates the polymerization (or hardening) of the composition. Such photopolymerizable compositions can be free radically polymerizable or cationically polymerizable. In other embodiments, the compositions are chemically hardenable, i.e., the compositions contain a chemical initiator (i.e., initiator system) that can polymerize, cure, or otherwise harden the composition without dependence on irradiation with actinic radiation. Such chemically hardenable compositions are sometimes referred to as "self-cure" compositions and may include glass ionomer cements (e.g., conventional and resin-modified glass ionomer cements), redox cure systems, and combinations thereof.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroboarate. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6- trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition. In some embodiments, the curable dental composition may be irradiated with ultraviolet (UV) rays. For this embodiment, suitable photoinitiators include those available under the trade designations IRGACURE and DAROCUR from Ciba Specialty Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

Hardening is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-1000 W/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

In some embodiments, such as when the dental composition is employed as a dental restorative (e.g. dental filling or crown) or an orthodontic adhesive, the dental composition typically comprises appreciable amounts of (e.g. nanoparticle) filler. Such compositions preferably include at least 40 wt-%, more preferably at least 45 wt-%, and most preferably at least 50 wt-% filler, based on the total weight of the composition. In some embodiments the total amount of filler is at most 90 wt-%, preferably at most 80 wt-%, and more preferably at most 75 wt-% filler.

Dental compositions suitable for use as dental adhesives can also include filler in amount of at least 1 wt-%, 2 wt-%, 3 wt-%, 4 wt-%, or 5 wt-% based on the total weight of the composition. For such embodiments, the total concentration of filler is at most 40 wt-%, preferably at most 20 wt-%, and more preferably at most 15 wt-% filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Non-acid-reactive inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. Nos. 6,387, 981 (Zhang et al.) and 6,572,693 (Wu et al.) as well as PCT International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. Nos. 7,090,721 (Craig et al.), 7,090,722 (Budd et al.), 7,156,911 (Kangas et al.), and 7,649,029 (Kolb et al.).

Examples of suitable organic filler particles include filled or unfilled pulverized polycarbonates, polyepoxides, poly (meth)acrylates and the like. Commonly employed dental filler particles are quartz, submicron silica, and non-vitreous microparticles of the type described in U.S. Pat. No. 4,503, 169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E.I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO 1041.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some favored embodiments, the nanoparticles are in the form of nanoclusters, i.e. a group of two or more particles associated by relatively weak intermolecular forces that cause the particles to clump together, even when dispersed in a hardenable resin.

Preferred nanoclusters can comprise a substantially amorphous cluster of non-heavy (e.g. silica) particles, and amorphous heavy metal oxide (i.e. having an atomic number greater than 28) particles such as zirconia. The particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like.

Suitable copolymerizable organometallic compounds may have the general formulas: $CH_2=C(CH_3)_m Si(OR)_n$ or $CH_2=C(CH_3)_m C=OOASi(OR)_n$; wherein m is 0 or 1, R is an alkyl group having 1 to 4 carbon atoms, A is a divalent organic linking group, and n is from 1 to 3. Preferred coupling agents include gamma-methacryloxypropyltrimethoxysilane, gamma-mercaptopropyltriethoxysilane, gamma-aminopropyltrimethoxysilane, and the like.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either subsequent to mixing with the monomers or after mixing. It is typically preferred to combine the organosilane surface treatment compounds with nanoparticles before incorporation into the resin. The required amount of surface modifier is dependant upon several factors such as particle size, particle type, modifier molecular wt, and modifier type. In general it is preferred that approximately a monolayer of modifier is attached to the surface of the particle.

The surface modified nanoparticles can be substantially fully condensed. Fully condensed nanoparticles (with the exception of silica) typically have a degree of crystallinity (measured as isolated metal oxide particles) greater than 55%, preferably greater than 60%, and more preferably greater than 70%. For example, the degree of crystallinity can range up to about 86% or greater. The degree of crystallinity can be determined by X-ray diffraction techniques. Condensed crystalline (e.g. zirconia) nanoparticles have a high refractive index whereas amorphous nanoparticles typically have a lower refractive index.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, (e.g. photobleachable or thermochromic) dyes, pigments, inhibitors, accelerators, viscosity modifiers, wetting agents, buffering agents, radical and cationic stabilizers (for example BHT,), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. Dental adhesives are also hardened by curing after applying the dental composition to the tooth. The method of treating an oral surface may comprise providing a dental article and adhering the dental article to an oral (e.g. tooth) surface. The dental article may comprise a cured composition comprising a polymerizable substituted saccharide compound as described herein. Alternatively, the dental article may be a conventional dental article (without a polymerizable substituted saccharide compound) adhered with an adhesive comprising a polymerizable substituted saccharide compound. Further, both the dental article and adhesive may both comprise a substituted saccharide compound.

In other embodiments, the compositions can be hardened (e.g., polymerized) into dental articles prior to applying. For example, a dental article such as a crown may be pre-formed from the hardenable dental composition described herein. Dental composite (e.g. crowns) artilces can be made from the curable composition described herein by casting the curable composition in contact with a mold and curing the composition. Alternatively, dental composite (e.g. crowns) article can be made by first curing the composition forming a mill blank and then mechanically milling the composition into the desired article.

Another method of treating a tooth surface comprises providing a dental composition as described herein wherein the composition is in the form of a (partially hardened) hardenable, self-supporting, malleable structure having a first semi-finished shape; placing the hardenable dental composition on a tooth surface in the mouth of a subject; customizing the shape of the hardenable dental composition; and hardening the hardenable dental composition. The customization can occur in the patient's mouth or on a model outside the patient mouth such as described in U.S. Pat. No. 7,674,850 (Karim et al.); incorporated herein by reference.

Methods of the present invention provide for the treatment of hard tissues, including human and animal tissues. Hard tissues include, for example, bone, teeth, and the component parts of teeth (e.g., enamel, dentin, and cementum).

When the dental adhesive compositions of the present invention include two or more parts, the two or more parts are preferably mixed just prior to or during the application process. Suitable mixing devices include, for example, static mixing devices.

In some embodiments, the adhesive composition can promote adhesion to both enamel and dentin. Further, the composition can be formulated to function as the etchant, primer, and adhesive to both enamel and dentin.

Once the adhesive composition of the present invention has been hardened, the composition is generally not readily removed. Methods of bonding a dental material to a dental structure surface preferably result in a bond to enamel or dentin (or preferably both), of at least 10 MPa, more preferably at least 15, MPa, and most preferably at least 20 MPa when tested according to the Notched Edge Shear Adhesion test method described in the examples. The shear bond strength is typically no greater than 60 MPa.

The dental restoration material described herein typically exhibits a flexural strength of at least 80 MPa, 90 MPa, or 100 MPa when tested according to the test method described in the examples. The flexural strength is typically no greater than 200 MPa Objects and advantages are further illustrated by the following examples, but the particular materials and amounts thereof recited in these examples, as well as other conditions and details, should not be construed to unduly limit this invention. Unless otherwise indicated, all parts and percentages are on a weight basis.

| | CAS# | Manufacturer |
|---|---|---|
| Starting Materials for Synthesis of Saccharide Compound | | |
| N-Methyl-N-Octanoyl Glucamide | 85316-98-9 | Calbiochem, La Jolla, CA |
| N-Octyl Glucamine | | Carbosynth Limited, Compton Berkshire, UK |
| IEM (2-isocyanatoethyl methacrylate) | 30674-80-7 | Showa Denko, Japan |
| Triethyl Amine | 121-44-8 | EMD Chemicals Inc., Gibbstown, NJ |
| Dibutyltin dilaurate | 77-58-7 | Alfa Aesar, Ward Hill, MA |
| MEK (methyl ethyl ketone) | 78-93-3 | Sigma-Aldrich |
| MEHQ (4-methoxyphenol) | 150-76-5 | Sigma-Aldrich, St. Louis, MO |
| $POCl_3$ (phosphorus(V) oxychloride) 99% | 10025-87-3 | Alfa Aesar |
| Methanol | 67-56-1 | Alfa Aesar |
| Acryloyl Chloride 96% | 814-68-6 | Alfa Aesar |
| THF (tetrahydrofuran, anhydrous) | 109-99-9 | Alfa Aesar |
| Ethyl Acetate | 141-78-6 | Alfa Aesar |
| DMF (dimethylformamide) | 68-12-2 | Sigma-Aldrich |
| Components of Hardenable Dental Composition | | |
| Ethylenically Unsaturated Free-Radically Polymerizable Monomers With Acid Functionality | | |
| HEMA-Phosphate (mixture of mono-, di-, tri-HEMA phosphate and tetraHEMA pyrophosphate) | | Prepared as described for HEMA-P in Columns 24-25 of U.S. Pat. No. 7,632,098 |
| MHP (6-methacryloxyhexyl phosphate) | | Prepared as described for MHP-B in Column 24 of U.S. Pat. No. 7,632,098 |

-continued

| | CAS# | Manufacturer |
|---|---|---|
| Ethylenically Unsaturated Free-Radically Polymerizable Monomers | | |
| Sorbitol DMA (sorbitol dimethacrylate) | | ABCR, Germany |
| BisGMA (Bisphenol A diglycidyl ether methacrylate) | 1565-94-2 | |
| Bis-EMA-6 (ethoxylated bisphenol A methacrylate as further described in U.S. Pat. No. 6,030,606) | | available from Sartomer as "CD541" |
| TEGDMA (triethyleneglycol dimethacrylate) | | |
| TMPTMA (trimethylolpropane trimethacrylate) | 3290-92-4 | Sigma-Aldrich |
| UDMA (diurethane dimethacrylate) | 72869-86-4 | Dajac Laboratories, Trevose, PA |
| HEMA (2-hydroxyethyl methacrylate) | | Sigma-Aldrich |
| DMAEMA (dimethylamino ethyl methacrylate) | 2867-47-2 | TCI America |
| VCP—Polymer made by reacting AA: ITA copolymer with sufficient IEM to convert 16 mole percent of the acid groups of the copolymer to pendent methacrylate groups according to the dry polymer preparation of Example 11 of U.S. Pat. No. 5,130,347. | | |
| BHT (2,6-di-tert-butyl-4-methylphenol) | 128-37-0 | Sigma-Aldrich or PMC Specialties, Inc. |
| Components of Photoinitator Package | | |
| CPQ (camphorquinone) | | Sigma-Aldrich |
| EDMAB (ethyl 4-(N,N-dimethylamino) benzoate) | | Sigma-Aldrich |
| DPIHFP (diphenyl iodonium hexafluorophosphate) | | Alpha Aesar |
| EDMOA (2-ethyl 9,10-dimethoxy anthracene) | 26708-04-3 | Sigma-Aldrich |
| phenylbis (2,4,6-trimethylbenzoyl) phosphine oxide, available under the trade designation "Irgacure 819" | 162881-26-7 | Ciba Specialty Chemicals Corp. |
| Inorganic Fillers | | |
| Zr/Si Nanocluster—Refers to silane-treated zirconia/silica nanocluster filler prepared essentially as described in U.S. Pat. No. 6,730,156 (Preparatory Example A (line 51-64) and Example B (column 25 line 65 through column 26 line 40). 20 nm Si Nanomer—Refers to silane-treated nano-sized silica having a nominal particle size of approximately 20 nanometers, prepared essentially as described in U.S. Pat. No. 6,572,693 B1, (column 21, lines 63-67 for Nanosized particle filler, Type #2. | | |

Test Methods:

1. Mass Spectrometry measurements were carried out with a Bruker Ultraflex II MALDI-TOF/TOF instrument with positive ionization and in reflector mode. Ion source (1) voltage was of 25 kV. Total studied mass range was of m/z 80-6000 Daltons. MALDI-MS/MS experiments were carried out in LIFT mode. The data was processed with Bruker FlexAnalysis 2.4 software.

Samples were dissolved in methanol prior to the analyses. MALDI matrix solution was 2,5-Dihydroxybenzoic acid (DHB) in THF at 25 mg/ml. 0.3 µl aliquots of sample solution, followed by the additions of 0.3 µl aliquot of the matrix solution were applied on a MALDI plate. 0.3 µl of methanol and 0.3 µl of MALDI matrix were applied for background spectra measurements.

2. Notched Edge Shear Adhesion Test Method (Cut Enamel and Dentin) Preparation of Test Teeth—Bovine incisal teeth were obtained from a local slaughterhouse, the roots cut off, and the pulp removed. The teeth, free of soft tissue, were embedded in circular acrylic disks so that the labial surfaces of the teeth were exposed. The embedded teeth were stored in deionized water in a refrigerator prior to use.

For testing on cut enamel or dentin, the embedded teeth were ground to expose a flat enamel or dentin surface using 120-grit sandpaper mounted on a lapidary wheel. Further grinding and polishing of the tooth surface was done using 320-grit sandpaper on the lapidary wheel. The teeth were continuously rinsed with water during the grinding process.

An adhesive test sample was applied with a dental applicator brush over the exposed labial tooth surface and light cured for 10 seconds with an XL 3000 dental curing light (3M Company, St. Paul, Minn.). A 2-mm thick Teflon mold with a hole approximately 2.38 mm in diameter was clamped to the embedded tooth such that the hole in the mold exposed the flattest available area of the adhesively prepared tooth surface. A composite material, FILTEK Z250 Universal Restorative (3M Company), was filled into the hole such that the hole was completely filled, but not overfilled, and light cured per manufacturer's directions to form a "button" that was adhesively attached to the tooth.

The finished test samples were stored in deionized water at 37 degree C. for approximately 24 hours prior to testing.

Sample Testing—The test samples were mounted in a holder clamped in the jaws of an Instron™. (Instron 4505, Instron Corp. Canton, Mass.) with the tooth surface oriented parallel to the direction of the pushing shear force. A metal fixture with a semicircular notched edge was attached to the Instron, and the notched edge was carefully fitted onto the button, flush with the tooth surface. The pushing shear force was started at a crosshead speed of 1 mm/min. The force in kilograms (kg) at which the bond failed was recorded, and this number was converted to a force per unit area (units of kg/cm$^2$ or MPa) using the known surface area of the button. Each reported value of adhesion to enamel or adhesion to dentin represents the average of 5 replicates.

3. Flexural Strength (FS) Test—Flexural Strength was measured according to the following test procedure. A composition sample was pressed at 65° C. in a preheated mold to form a 2-mm×2-mm×25-mm test bar. The bar was aged at room temperature for 24 hours and light cured for 90 seconds by exposure to two oppositely disposed VISILUX Model 2500 blue light guns (3M Co.). The bar was then post-cured for 180 seconds in a Dentacolor XS unit (Kulzer, Inc., Germany) light box, and sanded lightly with 600-grit sandpaper to remove flash from the molding process. After storing in distilled water at 37° C. for 24 hours, the Flexural Strength and Flexural Modulus of the bar were measured on an Instron tester (Instron 4505, Instron Corp., Canton, Mass.) according to ANSI/ADA (American National Standard/American Dental Association) specification No. 27 (1993) at a crosshead speed of 0.75 mm/minute. Eight bars of cured composite were prepared and measured with results reported in megapascals (MPa) as the average of the eight measurements.

Example 1

Synthesis of N-Methyl N-Octanoyl Glucamide Dimethacrylate

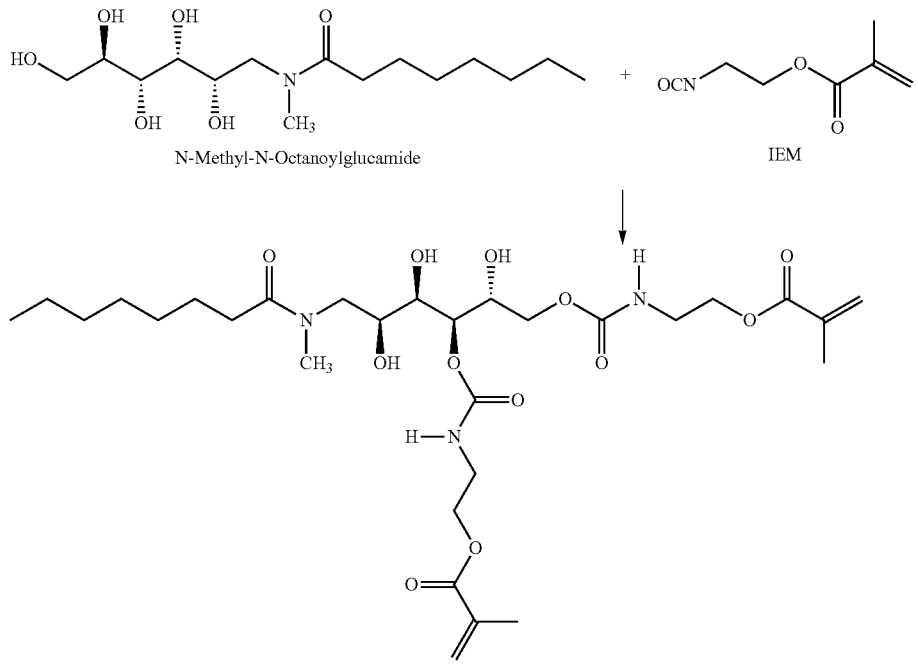

To a 250 ml round bottom flask was added N-Methyl-N-Octanoyl Glucamide (5.000 g, 15.57 mmol), MEK (80 ml), MEHQ (5 mg), and warm up to 60° C. until all solids were dissolved. IEM (4.8257 g, 31.13 mmol) was added dropwise, followed by dibutyltin dilaurate (1 ml, 1% solution in MEK). The reaction temperature was maintained at 60° C. for 8 hrs. The reaction mixture was then analyzed with infared analysis (IR) and thin layer chromatography (TLC). IR indicated no isocyanate signal (no IEM left). TLC (15% Methanol/85% Ethyl Acetate) showed no starting N-Methyl-N-Octanoyl Glucamide left. Vacuum evaporation of the solvent MEK yielded a clear liquid of polymerizable resin (9.9 g), which was used in the following dental compositions without further purification. NMR confirmed the structure depicted above was obtained.

Adhesive Formulations and Test Results

Dental adhesive formulations were prepared by combining and mixing the components until uniform. In all cases, water was the final component added. All units are in grams unless otherwise specified.

Example 2

Dental Adhesive

| Material | Weight (g) | Wt % |
|---|---|---|
| HEMA-Phosphate | 2.3625 | 40.61% |
| MHP | 0.7875 | 13.54% |
| Example 1 | 1.5 | 25.79% |
| TEGDMA | 0.175 | 3.01% |
| CPQ | 0.0925 | 1.59% |

-continued

| Material | Weight (g) | Wt % |
|---|---|---|
| EDMAB | 0.062 | 1.07% |
| EDMOA | 0.0095 | 0.16% |
| DFIHFP | 0.0245 | 0.42% |
| HEMA | 0.175 | 3.01% |
| VCP | 0.0519 | 0.89% |
| DI Water | 0.5765 | 9.91% |

Notched Edge Shear Bond Strength of Example 2

| Dentin (MPa) | Std. Dev. (MPa) | Cut-Enamel (MPa) | Std. Dev. (MPa) |
|---|---|---|---|
| 22.47 | 4.35 | 23.22 | 5.70 |

Examples 3-4

Dental Adhesives

| Material | Ex. C Wt (g) | Ex. C Wt-% | Ex. 3 Wt (g) | Ex. 3 Wt-% | Ex. 4 Wt (g) | Ex. 4 Wt-% |
|---|---|---|---|---|---|---|
| HEMA-Phosphate | 6.88 | 60.47% | 6.88 | 60.47% | 6.88 | 60.47% |
| MHP | 1.12 | 9.84% | 1.12 | 9.84% | 1.12 | 9.84% |
| Example 1 | 0 | 0% | 0.5 | 4.39% | 1.32 | 11.60% |
| TMPTMA | 0.68 | 5.98% | 0.68 | 5.98% | 0.68 | 5.98% |
| HEMA | 0.48 | 4.22% | 0.2982 | 2.62% | 0 | 0% |

| Material | Ex. C Wt (g) | Ex. C Wt-% | Ex. 3 Wt (g) | Ex. 3 Wt-% | Ex. 4 Wt (g) | Ex. 4 Wt-% |
|---|---|---|---|---|---|---|
| UDMA | 0.48 | 4.22% | 0.2982 | 2.62% | 0 | 0% |
| Sorbitol DMA | 0.36 | 3.16% | 0.2236 | 1.97% | 0 | 0% |
| CPQ | 0.1856 | 1.63% | 0.1856 | 1.63% | 0.1856 | 1.63% |
| EDMAB | 0.1238 | 1.09% | 0.1238 | 1.09% | 0.1238 | 1.09% |
| EDMOA | 0.0186 | 0.16% | 0.0186 | 0.16% | 0.0186 | 0.16% |
| DFIHFP | 0.0496 | 0.44% | 0.0496 | 0.44% | 0.0496 | 0.44% |
| DI Water | 1.00 | 8.79% | 1.00 | 8.79% | 1.00 | 8.79% |

Notched Edge Shear Bond Strength of Examples 3 & 4

| | Dentin (MPa) | Std. Dev. (MPa) | Wt-% Example 1 |
|---|---|---|---|
| Control | 7.52 | 5.73 | 0 |
| Ex. 3 | 20.18 | 3.45 | 5 |
| Ex. 4 | 20.32 | 2.64 | 13.2 |

Example 5

Synthesis of N-Octyl Acryloyl Glucamide

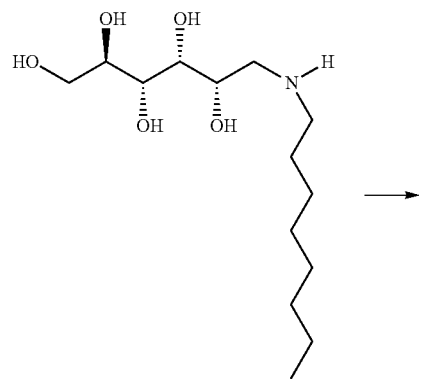

N-Octyl Glucamine

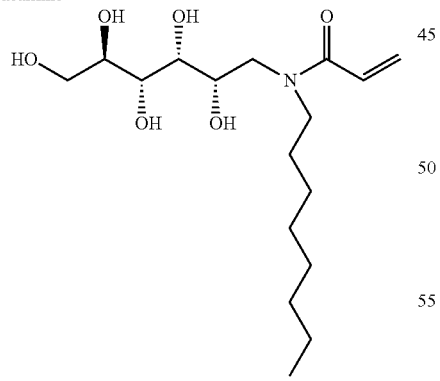

To a 500 ml round bottom flask was added N-Octyl Glucamine (5.00 g), MEHQ (10 mg), Methanol (120 ml), and triethyl Amine (3.80 g). It was heated up to 60° C. under nitrogen, and with magnetic stirring. After all the solids were dissolved, the temperature was lowered to 50° C. Acryloyl chloride (3.08 g) in THF (20 ml) was added dropwise. After 5 hrs reacting at 50° C., TLC (15% Methanol/85% Ethyl Acetate) showed no starting N-Octyl Glucamine left. After vacuum evaporating of the solvents, 10 g of solids were obtained; further purification was conducted with a column chromatography (Silica gel 60 (40-63 Microns available form EM Sciences, Gibbstown, N.J.); 15% Methanol/85% Ethyl Acetate), and N-Octyl Acryloyl Glucamide (4.65 g white solid, 78.6% yield) was obtained. $^1$H NMR confirmed the structure depicted above was obtained.

Example 6

Dental Adhesive

| Material | Weight (g) | Wt % |
|---|---|---|
| HEMA-Phosphate | 2.3625 | 40.61% |
| MHP | 0.7875 | 13.54% |
| Example 1 | 1.0 | 17.19% |
| Example 5 | 0.5 | 8.60% |
| TEGDMA | 0.175 | 3.01% |
| CPQ | 0.0925 | 1.59% |
| EDMAB | 0.062 | 1.07% |
| EDMOA | 0.0095 | 0.16% |
| DFIHFP | 0.0245 | 0.42% |
| HEMA | 0.175 | 3.01% |
| VCP | 0.0519 | 0.89% |
| DI Water | 0.5765 | 9.91% |

Notched Edge Bond Strength of Example 6

| Dentin (MPa) | Std. Dev. (MPa) | Cut-Enamel (MPa) | Std. Dev. (MPa) |
|---|---|---|---|
| 16.52 | 1.77 | 23.76 | 1.43 |

Example 7

Synthesis of N-Octyl Acryloyl Glucamide Phosphates

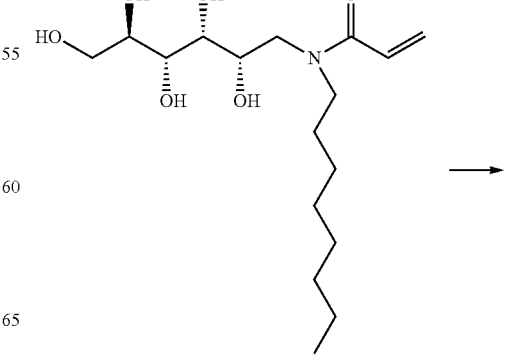

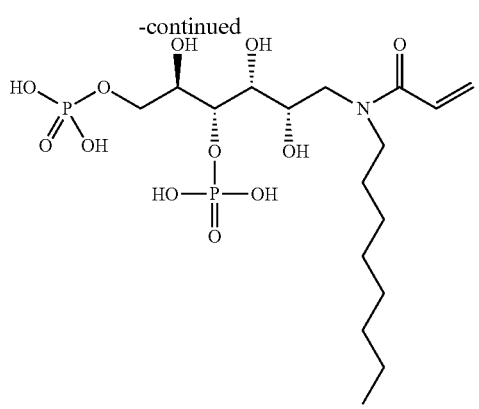

To a 250 ml 3-neck round bottom flask was added THF (Anhydrous, 40 ml), POCl₃ (2.2094 g), and this mixture was cooled down to −50° C. in an IPA-Dry Ice bath under nitrogen and magnetic stirring. To a dropping funnel, was added N-Octyl Acryloyl Glucamide of Example 5 (1.0000 g), THF (Anhydrous, 50 ml), and triethyl amine (1.4581 g); this solution was added dropwise to the 250 ml round bottom flask in 1 hour while maintaining the IPA-Dry Ice bath temperature at −40° C. After the addition, the IPA-Dry Ice bath temperature was maintained between −40° C. and −30° C. for another 2 hours. The IPA-Dry Ice bath was then let warmed up to 0° C., and DI water (0.5187 g) was added together with triethyl amine (2.9161 g) to the reaction mixture. This IPA-Dry Ice bath was then removed, to let the reaction continued for 12 hours at RT. TLC (15% Methanol/85% Ethyl Acetate) analysis of the reaction mixture showed no starting N-Octyl Acryloyl Glucamide left. White crystals (Triethyl amine-HCl salt) formed in the reaction mixture were filtered off. The resulting solution was gradually concentrated (Rotary Evaporator, water aspirator), and additional white crystals formed were filtered off. A final clear viscous liquid (1.50 g) was obtained. Mass Spectrometry indicated the structure depicted above was obtained.

Example 8

Dental Adhesive

| Material | Weight (g) | Wt % |
|---|---|---|
| HEMA-Phosphate | 2.3625 | 40.61% |
| Example 7 | 0.7875 | 13.54% |
| Example 1 | 1.5 | 25.79% |
| TEGDMA | 0.175 | 3.01% |
| CPQ | 0.0925 | 1.59% |
| EDMAB | 0.062 | 1.07% |
| EDMOA | 0.0095 | 0.16% |
| DFIHFP | 0.0245 | 0.42% |
| HEMA | 0.175 | 3.01% |
| VCP | 0.0519 | 0.89% |
| DI Water | 0.5765 | 9.91% |

Notched Edge Bond Strength of Example 8

| Dentin (MPa) | Std. Dev. (MPa) | Cut-Enamel (MPa) | Std. Dev. (MPa) |
|---|---|---|---|
| 17.17 | 0.98 | 21.39 | 2.90 |

Example 9

Synthesis of Di-methacrylate

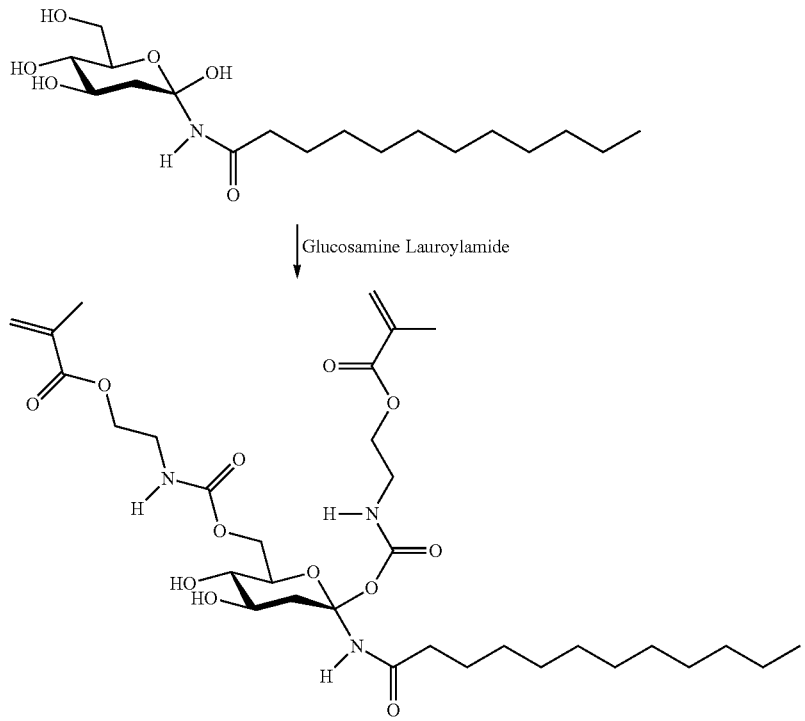

To a 500 ml 3neck round bottom flask, was added glucosamine lauroylamide (5.00 g), made via reference procedure [1] cited below; DMF (200 ml), HEMQ (10 mg), and heated up to 70° C. under nitrogen. After all the solids were dissolved, IEM (4.2936 g) and dibutyltin dilaurate (2 ml of 1% MEK solution) were added, and the reaction temperature was kept at 70° C. for 7 hrs. The reaction mixture was then analyzed with IR and TLC. TLC (15% methanol, 85% ethyl acetate) showed no glucosamine lauroylamide starting material remained. IR showed no —NCO groups remained. Mass Spectrometry indicated the structure depicted above was obtained. After vacuum evaporating of the solvents, a white solid product as obtained that was used without further purification.

[1] Inouye et al., JACS, 1956, V78, pp. 4722-4724.

Dental Adhesive Example 10

| Material | Weight (g) | Wt % |
|---|---|---|
| HEMA-Phosphate | 2.3625 | 40.61% |
| MHP | 0.7875 | 13.54% |
| Example 1 | 1.35 | 23.21% |
| Example 9 | 0.15 | 2.58% |
| TEGDMA | 0.175 | 3.01% |
| CPQ | 0.0925 | 1.59% |
| EDMAB | 0.062 | 1.07% |
| EDMOA | 0.0095 | 0.16% |
| DFIHFP | 0.0245 | 0.42% |
| HEMA | 0.175 | 3.01% |
| VCP | 0.0519 | 0.89% |
| DI Water | 0.5765 | 9.91% |

Notched Edge Shear Bond Strength of Dental Adhesive Example 10

| Dentin (MPa) | Std. Dev. (MPa) | Cut-Enamel (MPa) | Std. Dev. (MPa) |
|---|---|---|---|
| 18.07 | 0.64 | 24.01 | 3.39 |

Example 11

Dental Composite

| Material | Weight (g) | Wt-% |
|---|---|---|
| Example 1 | 0.3450 | 2.28% |
| BisGMA | 0.7938 | 5.25% |
| TEGDMA | 0.0882 | 0.58% |
| UDMA | 1.1115 | 7.35% |
| Bis-EMA6 | 1.1115 | 7.35% |
| CPQ | 0.0060 | 0.04% |
| DFIHFP | 0.0177 | 0.12% |
| EDMAB | 0.0355 | 0.23% |
| BHT | 0.0053 | 0.04% |
| TINUVIN | 0.0532 | 0.35% |
| Zr/Si Nano-Cluster | 10.3950 | 68.76% |
| 20 nm Si Nanomer | 1.1550 | 7.64% |

Flexural Strength

| | Flexural Strength (MPa) | Flexural Modulus (MPa) |
|---|---|---|
| Example 11 | 119 ± 23 | 12717 ± 643 |

Example 12

Dental Adhesive

| Material | Control | Ex. 12 |
|---|---|---|
| HEMA-Phosphate | 68.39 wt-% | 68.39 wt-% |
| BisGMA | 9.77% | 0.00% |
| Example 1 | 0.00% | 9.77% |
| CPQ | 0.96% | 0.96% |
| EDMAB | 0.72% | 0.72% |
| Irgacure 819 | 0.08% | 0.08% |
| BHT | 0.08% | 0.08% |
| DI water | 14.84% | 14.84% |
| HEMA | 4.95% | 4.95% |
| VCP | 0.20% | 0.20% |
| MEHQ | 0.01% | 0.01% |

The pH of this composition was measured and determined to be 0.

Adhesive Shear Bond Strength of Example 12

| | Dentin (MPa) | Std. Dev. (MPa) |
|---|---|---|
| Control | 12.00 | 11.76 |
| Example 12 | 22.18 | 10.71 |

Example 13

Dental Adhesive

Preparation of THPICTHS

THPICTHS was prepared from trigylcidyl isocyanurate and mono-(2-methacryloxyethyl)succincate as described in U.S. Provisional Application Ser. No. 61/319,534, filed Mar. 31, 2010; incorporated herein by reference.

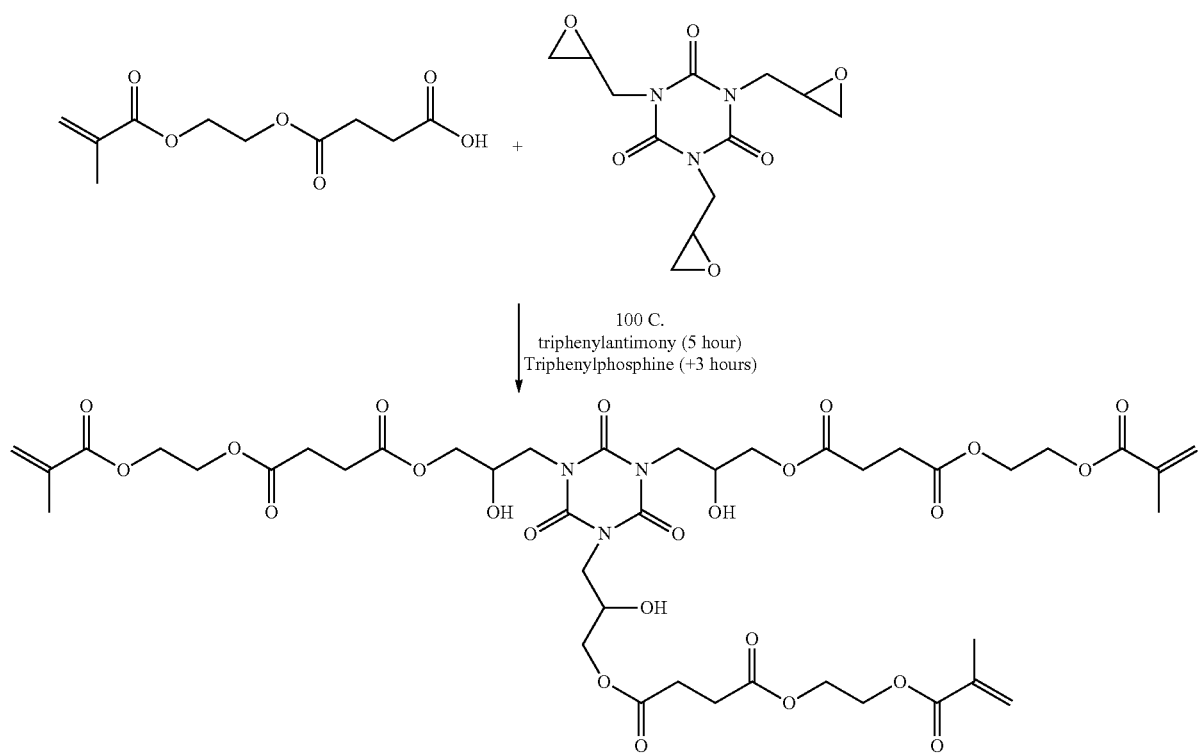

| Material | Control |
|---|---|
| HEMA-Phosphate | 68.39 wt-% |
| BisGMA | 9.77% |
| CPQ | 0.96% |
| EDMAB | 0.72% |
| Irgacure 819 | 0.08% |
| BHT | 0.08% |
| DI water | 14.84% |
| HEMA | 4.95% |
| VCP | 0.20% |
| MEHQ | 0.01% |

| Material | Example 13 |
|---|---|
| HEMA-Phosphate | 40.52% |
| Example 1 | 11.30% |
| THPICTHS | 11.30% |
| TEGDMA | 2.64% |
| CPQ | 1.59% |
| EDMAB | 1.06% |
| EDMOA | 0.16% |
| DPIHFP | 0.42% |
| DI water | 10.00% |
| HEMA | 3.00% |
| VCP | 1.00% |
| MHP | 13.50% |
| DMAEMA | 3.50% |

The pH of this composition was measured and determined to be less than 1.

Adhesive Shear Bond Strength of Example 13

| | Dentin (MPa) | Std. Dev. (MPa) |
|---|---|---|
| Control | 6.93 | 10.88 |
| Example 13 | 15.46 | 7.63 |

Example 14

Synthesis of bis-2-(2-methacryloyloxy)-ethylaminocarbonyl adduct of N-methyl-N-[(2S,3R,4R,5R)-2,3,4,5,6-pentahydroxyhexyl]docosanamide Synthesis of N-methyl-N-[(2S,3R,4R,5R)-2,3,4,5,6-pentahydroxyhexyl]docosanamide Intermediate N-Methyl glucamine (1.95 g, 10.0 mmol) was dissolved in 10 mL of 1.00 N sodium hydroxide solution and 10 mL of tetrahydrofuran. Docosanoyl chloride (3.58 g, 10.0 mmol) was then added to the rapidly stirred solution followed by another 20 mL portion of tetrahydrofuran. After stirring for 60 min, the thick reaction mixture was placed on a rotary evaporator and tetrahydrofuran was removed under reduced pressure. The resulting thick slurry was filtered, washed with water and dried with suction to give a waxy white solid. Chromatography (SiO$_2$, 15%-30% MeOH/CHCl$_3$) yielded 1.52 g of the following compound as a waxy solid.

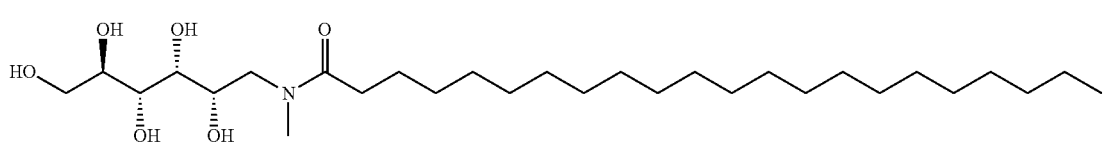

Bis-2-(2-methacryloyloxy)-ethylaminocarbonyl adduct of N-methyl-N-[(2S,3R,4R,5R)-2,3,4,5,6-pentahydroxyhexyl]docosanamide N-methyl-N-[(2S,3R,4R,5R)-2,3,4,5,6-pentahydroxyhexyl]docosanamide (200 mg, 0.387 mmol) was dissolved in 10 mL of tetrahydrofuran at 50° C. 2-Isocyantoethyl methacrylate (IEM, 109 mL, 0.772 mmol) was added followed by a catalytic amount of dibutyltin dilaurate. After stirring for 3 days at ambient temperature, the reaction mixture was concentrated under reduced pressure. Chromatography (SiO$_2$, 2%-10% MeOH/CHCl$_3$) yielded 86 mg of the following compound.

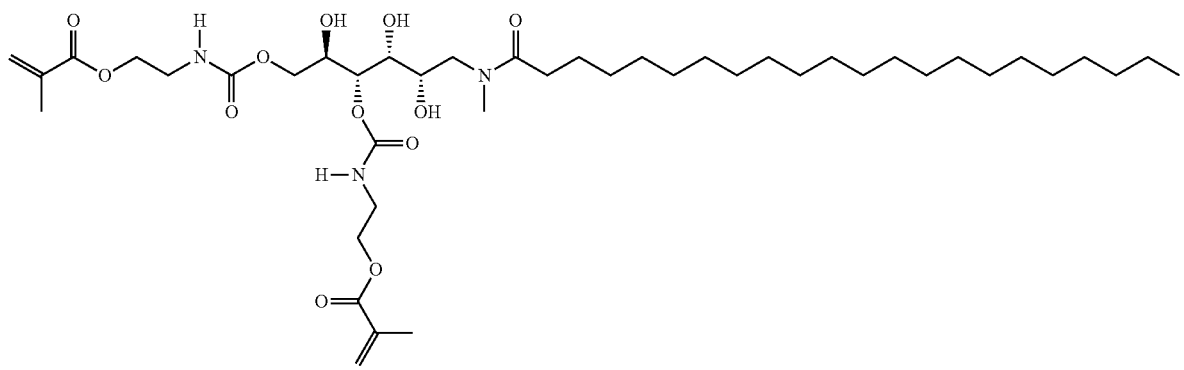 [SMILES: C=C(C)C(=O)OCCNC(=O)OC[C@@H](O)[C@@H](OC(=O)NCCOC(=O)C(=C)C)[C@H](O)[C@@H](O)CN(C)C(=O)CCCCCCCCCCCCCCCCCCCCC]

Example 15

Dental Composite

| Material | Weight (g) | Wt % |
| --- | --- | --- |
| MEGA22DIEM | 0.3450 | 2.28% |
| BisGMA | 0.7938 | 5.25% |
| TEGDMA | 0.0882 | 0.58% |
| UDMA | 1.1115 | 7.35% |
| Bis-EMA6 | 1.1115 | 7.35% |
| CPQ | 0.0060 | 0.04% |
| DFIHFP | 0.0177 | 0.12% |
| EDMAB | 0.0355 | 0.23% |
| BHT | 0.0053 | 0.04% |
| TINUVIN | 0.0532 | 0.35% |
| Zr/Si Nano-Cluster | 10.3950 | 68.76% |
| 20 nm Si Nanomer | 1.1550 | 7.64% |

Flexural Strength

| | Flexural Strength (MPa) | Flexural Modulus (MPa) |
| --- | --- | --- |
| Example 15 | 120 ± 014 | 8963 ± 972 |

What is claimed is:

1. A substituted saccharide amide compound having the formula $$R_3OCHH_2 \text{---} [CHOR_3]_n \text{---} CH_2NR_1R_2$$

wherein R$_1$ is a hydrophobic group;
R$_2$ is a free-radically polymerizable group;
R$_3$ is independently hydrogen or an acidic group and at least one of the R$_3$ groups is an acidic group; and
and n is an integer ranging from 1 to 4.

2. The substituted saccharide compound of claim 1 wherein hydrophobic group renders the substituted saccharide compound sufficiently lipophilic such that the substituted saccharide amide compound has an HLB decrease of at least 2 relative to the same unsubstituted saccharide amide compound.

3. A substituted saccharide compound having the general formula

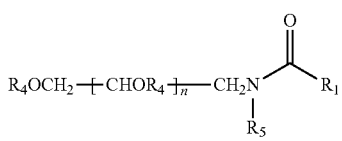

wherein R$_1$ is a hydrophobic group;
R$_4$ is independently hydrogen, an acidic group, or -L-R$^2$ wherein L is a linking group and R$^2$ is a free-radically polymerizable group with the proviso that at least one R$_4$ is -L-R$_2$;
R$_5$ is hydrogen or a C$_1$-C$_4$ alkyl group; and
and n is an integer ranging from 1 to 4.

4. The substituted saccharide compound of claim 3 wherein at least two R$_4$ groups are -L-R$^2$.

5. A substituted saccharide compound having the general formula

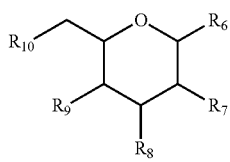

wherein
one of $R_6$-$R_{10}$ is

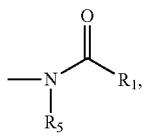

wherein $R_5$ is hydrogen or a $C_1$-$C_4$ alkyl group and $R_1$ is a hydrophobic group;
at least one of $R_6$-$R_{10}$ is O-L-$R_2$, wherein O is oxygen, L is a linking group, and $R_2$ is a free-radically polymerizable group; and
the remaining $R_6$-$R_{10}$ are OH or an acidic group.

10. The saccharide compound of claim 3 wherein at least one $R_4$ is an acidic groups selected from phosphoric, phosphonic, sulfuric, and carboxylic acidic groups.

11. A polymerizable dental composition comprising the substituted saccharide amide compound according to claim 1.

12. The polymerizable dental composition of claim 11 wherein the dental composition further comprises at least one other ethylenically unsaturated monomer selected from ethylenically unsaturated compounds with acid functionality, ethylenically unsaturated compounds without acid functionality, and combinations thereof.

13. The polymerizable dental composition of claim 11 wherein the dental composition is free of ethylenically unsaturated monomer derived from bisphenol A.

14. The polymerizable dental composition of claim 11 wherein the composition is suitable for use as a sealant, adhesive, cement, flowable composite restoration, or dental restoration material.

15. The dental restoration material of claim 14 further comprising at least 40 wt-% of nanocluster filler.

16. The substituted saccharide compound of claim 3 wherein the substituted saccharide compound comprises at least two free-radically polymerizable groups.

17. A substituted saccharide compound of claim 3 wherein the compound is

6. The substituted saccharide compound of claim 5 wherein at least two of $R_6$-$R_{10}$ are O-L-$R^2$.

7. The substituted saccharide compound of claim 5 wherein the remaining $R_6$—$R_{10}$ are OH.

8. The substituted saccharide compound of claim 1 wherein the hydrophobic group is a $C_5$ to $C_{26}$ alkyl group.

9. The saccharide compound of claim 1 wherein the free-radically polymerizable group is a (meth)acrylate group.

18. The substituted saccharide compound of claim 8 wherein the hydrophobic group is an alkyl group comprising at least 6 carbon atoms.

19. The substituted saccharide compound of claim 9 wherein the (meth)acrylate group is bonded to the saccharide amide via a urethane linkage.

20. The saccharide compound of claim 5 wherein at least one $R_6$-$R_{10}$ is an acidic group selected from phosphoric, phosphonic, sulfuric, and carboxylic acidic groups.

21. The saccharide compound of claim 1 wherein the acidic group is selected from phosphoric, phosphonic, sulfuric, and carboxylic acidic groups.

22. The saccharide compound of claim 1 wherein the compound is

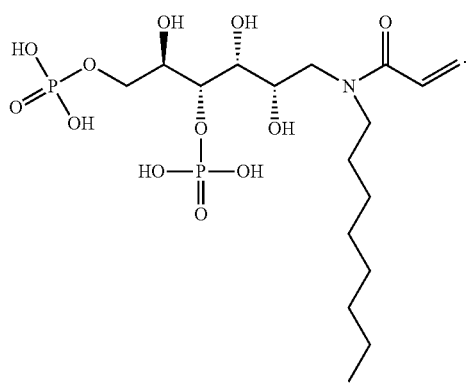 [SMILES: C=CC(=O)N(CCCCCCCC)C[C@H](O)[C@@H](O)[C@H](OP(=O)(O)O)[C@H](O)COP(=O)(O)O]

23. The substituted saccharide compound of claim 3 wherein hydrophobic group renders the substituted saccharide compound sufficiently lipophilic such that the substituted saccharide amide compound has an HLB decrease of at least 2 relative to the same unsubstituted saccharide amide compound.

24. The substituted saccharide compound of claim 3 wherein the hydrophobic group is a $C_5$ to $C_{26}$ alkyl group.

25. The substituted saccharide compound of claim 24 wherein the hydrophobic group is an alkyl group comprising at least 6 carbon atoms.

26. The saccharide compound of claim 3 wherein the free-radically polymerizable group is a (meth)acrylate group.

27. The substituted saccharide compound of claim 26 wherein the (meth)acrylate group is bonded to the saccharide amide via a urethane linkage.

28. A polymerizable dental composition comprising the substituted saccharide amide compound according to claim 3.

29. The polymerizable dental composition of claim 28 wherein the dental composition further comprises at least one other ethylenically unsaturated monomer selected from ethylenically unsaturated compounds with acid functionality, ethylenically unsaturated compounds without acid functionality, and combinations thereof.

30. The polymerizable dental composition of claim 28 wherein the dental composition is free of ethylenically unsaturated monomer derived from bisphenol A.

31. The polymerizable dental composition of claim 28 wherein the composition is suitable for use as a sealant, adhesive, cement, flowable composite restoration, or dental restoration material.

32. The dental restoration material of claim 31 further comprising at least 40 wt-% of nanocluster filler.

33. The substituted saccharide compound of claim 5 wherein hydrophobic group renders the substituted saccharide compound sufficiently lipophilic such that the substituted saccharide amide compound has an HLB decrease of at least 2 relative to the same unsubstituted saccharide amide compound.

34. The substituted saccharide compound of claim 5 wherein the hydrophobic group is a $C_5$ to $C_{26}$ alkyl group.

35. The substituted saccharide compound of claim 34 wherein the hydrophobic group is an alkyl group comprising at least 6 carbon atoms.

36. The saccharide compound of claim 5 wherein the free-radically polymerizable group is a (meth)acrylate group.

37. The substituted saccharide compound of claim 36 wherein the (meth)acrylate group is bonded to the saccharide amide via a urethane linkage.

38. The substituted saccharide compound of claim 5 wherein the substituted saccharide compound comprises at least two free-radically polymerizable groups.

39. A polymerizable dental composition comprising the substituted saccharide amide compound according to claim 5.

40. The polymerizable dental composition of claim 39 wherein the dental composition further comprises at least one other ethylenically unsaturated monomer selected from ethylenically unsaturated compounds with acid functionality, ethylenically unsaturated compounds without acid functionality, and combinations thereof.

41. The polymerizable dental composition of claim 39 wherein the dental composition is free of ethylenically unsaturated monomer derived from bisphenol A.

42. The polymerizable dental composition of claim 39 wherein the composition is suitable for use as a sealant, adhesive, cement, flowable composite restoration, or dental restoration material.

43. The dental restoration material of claim 42 further comprising at least 40 wt-% of nanocluster filler.

44. A substituted saccharide compound of claim 5 wherein the compound is

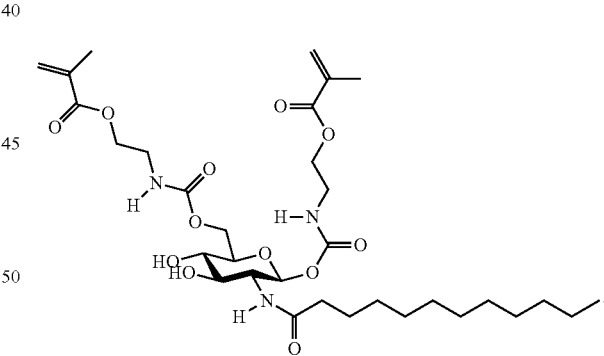

* * * * *

UNITED STATES PATENT AND TRADEMARK OFFICE
CERTIFICATE OF CORRECTION

PATENT NO. : 8,557,893 B2
APPLICATION NO. : 13/813673
DATED : October 15, 2013
INVENTOR(S) : Jie Yang et al.

It is certified that error appears in the above-identified patent and that said Letters Patent is hereby corrected as shown below:

Title Page 2, Column 1
Line 2, Delete "Argiculture," and insert -- Agriculture, --, therefor.

Title Page 2, Column 2
Line 6, Delete "ver" and insert -- vera --, therefor.
Line 24, Delete "Cariology," and insert -- Cardiology, --, therefor.

In the Specification
Column 2
Line 53-54, Delete "crosslinking" and insert -- crosslinking. --, therefor.

Column 5
Line 8, Delete "athe" and insert -- the --, therefor.
Line 38-39, Delete "cyclopenyl," and insert -- cyclopentyl, --, therefor.

Column 7
Line 3, Delete "$R^2$" and insert -- $R_2$ --, therefor.

Column 8
Line 2, Delete "$R^2$" and insert -- $R_2$ --, therefor.
Line 56, Delete "sacharride" and insert -- saccharide --, therefor.
Line 59-60, Delete "sacharride" and insert -- saccharide --, therefor.

Column 9
Line 17, Delete "saccaride" and insert -- saccharide --, therefor.
Line 52, Delete "sorbital" and insert -- sorbitol --, therefor.
Line 54, Delete "sorbital" and insert -- sorbitol --, therefor.
Line 65, Delete "hydroxylethyl" and insert -- hydroxyethyl --, therefor.

Signed and Sealed this
Thirtieth Day of September, 2014

Michelle K. Lee
*Deputy Director of the United States Patent and Trademark Office*

Column 11
Line 9, Delete "bisphenolA" and insert -- bisphenol A --, therefor.

Column 12
Line 31, Delete "sorbital" and insert -- sorbitol --, therefor.
Line 34, Delete "The)" and insert -- The --, therefor.

Column 14
Line 40, Delete "tetrafluoroboarate." and insert -- tetrafluoroborate. --, therefor.

Column 15
Line 18, Delete "Specialty" and insert -- Speciality --, therefor.

Column 19
Line 3, Delete "BHT,)," and insert -- BHT), --, therefor.
Line 48, Delete "artilces" and insert -- articles --, therefor.

Column 20
Line 29, Delete "MPa" and insert -- MPa. --, therefor.

Column 21
Line 27, Delete "Photoinitator" and insert -- Photoinitiator --, therefor.

Column 23
Line 40, Delete "infared" and insert -- infrared --, therefor.

Column 29
Line 1, Delete "3neck" and insert -- 3-neck --, therefor.

Column 30
Line 64, Delete "trigylcidyl" and insert -- triglycidyl --, therefor.

Column 33
Line 16, Delete "Isocyantoethyl" and insert -- Isocyanoethyl --, therefor.

In the Claims
Column 34

Line 14, In Claim 1, delete " $R_3OCHH_2\!\!-\!\!\left[\!-\!CHOR_3\!-\!\right]\!-\!CH_2NR_1R_2$ " and insert -- $R_3OCH_2\!-\!\left[\!-\!CHOR_3\!-\!\right]_n\!-\!CH_2NR_1R_2$ --, therefor.
Line 18-19, In Claim 1, delete "and and" and insert -- and --, therefor.
Line 56, In Claim 3, delete "$R^{2}$" and insert -- $R_2$ --, therefor.
Line 61-62, In Claim 3, delete "and and" and insert -- and --, therefor.
Line 65, In Claim 4, delete "$R^{2}$" and insert -- $R_2$ --, therefor.

CERTIFICATE OF CORRECTION (continued)
U.S. Pat. No. 8,557,893 B2

Column 35
Line 59, In Claim 6, delete "$R^{2}$" and insert -- $R_2$ --, therefor.
Line 62, In Claim 7, delete "$R_6$—$R_{10}$" and insert -- $R_6$-$R_{10}$ --, therefor.

Column 35-36
Line 25-35,

In Claim 17, delete " 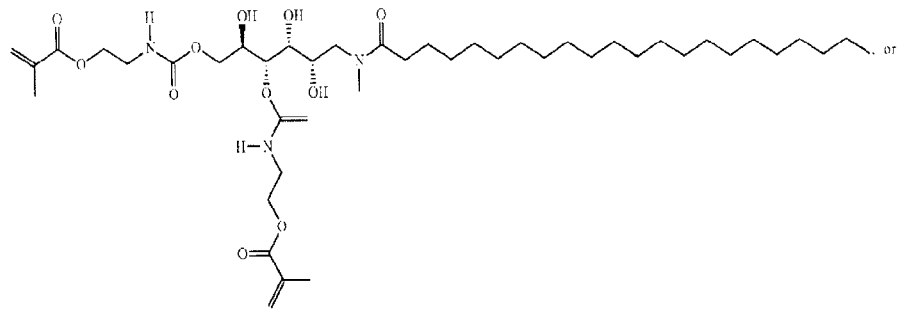 "
and insert

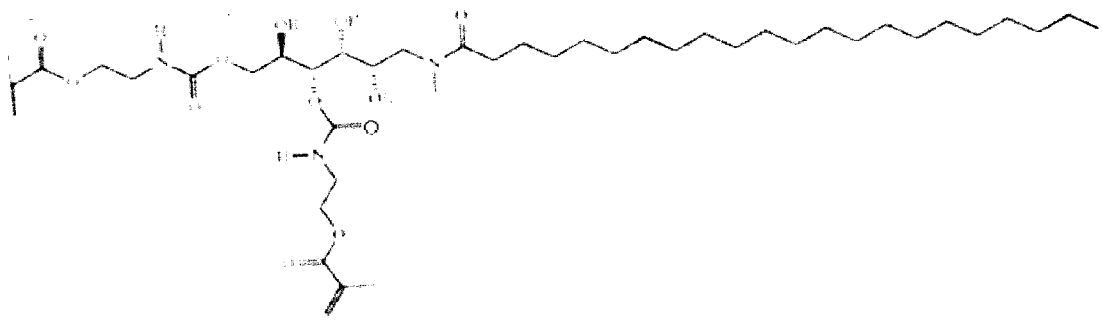

-- --,
therefor.